United States Patent [19]

Holland et al.

[11] 4,237,276

[45] Dec. 2, 1980

[54] BICYCLIC LACTONE INTERMEDIATES FOR 16-SUBSTITUTED PROSTAGLANDINS

[75] Inventors: George W. Holland, North Caldwell; Jane L. Jernow, Verona; Perry Rosen, North Caldwell, all of N.J.

[73] Assignee: Hoffmann-La Roche Inc., Nutley, N.J.

[21] Appl. No.: 50,267

[22] Filed: Jun. 19, 1979

Related U.S. Application Data

[60] Division of Ser. No. 847,881, Nov. 2, 1977, which is a continuation-in-part of Ser. No. 745,257, Dec. 8, 1976, Pat. No. 4,112,225, which is a continuation-in-part of Ser. No. 683,576, May 5, 1976, abandoned, which is a continuation-in-part of Ser. No. 480,458, Jun. 18, 1974, Pat. No. 4,052,446, which is a continuation-in-part of Ser. No. 386,117, Aug. 6, 1973, abandoned.

[51] Int. Cl.$^3$ .............................................. C07D 307/93
[52] U.S. Cl. .............................. 542/426; 260/343.3 P
[58] Field of Search .................. 260/343.3 P; 542/426

[56] References Cited

U.S. PATENT DOCUMENTS

| 3,959,263 | 5/1976 | Abraham et al. | 260/343.3 P |
|---|---|---|---|
| 3,993,688 | 11/1976 | Jernow et al. | 260/343.3 P |
| 4,001,281 | 1/1977 | Kienzle et al. | 260/343.3 P |
| 4,026,909 | 5/1977 | Yankee | 260/343.3 P |
| 4,029,693 | 6/1977 | Bundy et al. | 260/343.3 P |

FOREIGN PATENT DOCUMENTS

2437622  2/1975  Fed. Rep. of Germany .... 260/343.3 P

*Primary Examiner*—Henry R. Jiles
*Assistant Examiner*—Jane T. Fan
*Attorney, Agent, or Firm*—Jon S. Saxe; Bernard S. Leon; William H. Epstein

[57] ABSTRACT

A process for producing optically active 16-substituted prostaglandins and new 16-substituted prostaglandins produced thereby which are useful as cardiovascular agents and as agents for inducing labor in pregnant females and for the termination of pregnancy.

6 Claims, No Drawings

BICYCLIC LACTONE INTERMEDIATES FOR 16-SUBSTITUTED PROSTAGLANDINS

CROSS REFERENCE TO RELATED APPLICATIONS

This application is a divisional application of Ser. No. 847,881 filed Nov. 2, 1977, which in turn is a continuation-in-part application of Ser. No. 745,257 filed Dec. 8, 1976, now U.S. Pat. No. 4,112,225, which in turn is a continuation-in-part application of Ser. No. 683,576 filed May 5, 1976, now abandoned, which in turn is a continuation-in-part application of Ser. No. 480,458 filed June 18, 1974, now U.S. Pat. No. 4,052,446, which in turn is a continuation-in-part application of Ser. No. 386,117 filed Aug. 6, 1973, now abandoned.

SUMMARY OF THE INVENTION

In accordance with this invention, a new process has been discovered for preparing prostaglandin active compounds of the formula:

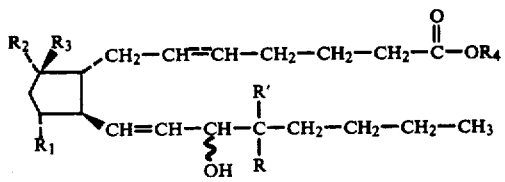

wherein $R_4$ is hydrogen or lower alkyl, $R_2$ is hydroxy; $R_3$ is hydrogen or taken together with $R_2$ forms oxo; $R_1$ is hydrogen, lower alkyl, $CH_2OR_1'$; or $-COOR_1'$; $R_1'$ is hydrogen or lower alkyl; R is fluoro, lower alkyl or trifluoromethyl; R', is hydrogen, fluoro or lower alkyl; and the dotted bond can be optionally hydrogenated;
from a compound of the formula

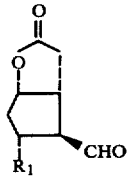

wherein $R_1$ is as above.

This process is extremely valuable in preparing a compound of formula I in their optically active form.

Among the compounds of I are the novel compounds

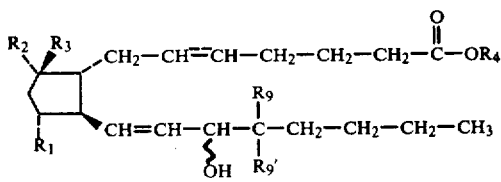

wherein $R_1$, $R_2$, $R_3$ and $R_4$ are as above, $R_9$ is trifluoromethyl or fluoro and $R_9'$ is lower alkyl, hydrogen and fluoro with the proviso that when $R_9'$ is lower alkyl or hydrogen, $R_9$ is trifluoromethyl and the dotted bond can be optionally hydrogenated; and their optically active antipodes. The compound of formula I-A and their optically active antipodes are also novel compounds. The compounds of formula I-A have cardiovascular activity, induce labor in pregnant females; are useful for terminating pregnancies and for combatting gastrohyperacidity. The compounds of formula I-A are also useful as bronchodilators and have anti-ulcerogenic properties.

DETAILED DESCRIPTION OF THE INVENTION

As used throughout this application, the term "lower alkyl" includes both straight chain and branched chain alkyl groups having from 1 to 7 carbon atoms such as methyl and ethyl. As also used herein, the term "lower alkanoic acids" comprehends an alkanoic acid of 1 to 7 carbon atoms such as formic acid and acetic acid. As further used herein, the term "halogen" or "halo", unless otherwise stated, comprehends fluorine, chlorine, bromine and iodine.

In the process of this invention, all compounds having one or more asymmetric carbon atoms can be produced as racemic mixtures. These racemic mixtures which are obtained can be resolved at the appropriate steps in the process of this invention by methods well known in the art discussed more fully below, whereupon subsequent products may be obtained as the corresponding optically pure enantiomers.

In the pictorial representation of the compounds given throughout this application, a thickened taper line ( ▼ ) indicated a substituent which is in the beta-orientation (above the plane of the molecule), a dotted line (---) indicates a substituent which is in the alpha-orientation (below the plane of the molecule) and a wavy line (∿) indicates a substituent which is in either the alpha- or beta-orientation or mixtures of these isomers. It is to be understood that the pictorial representations of the compounds given throughout the specification are set forth for convenience and are to be construed as inclusive of other forms including enantiomers and racemates and are not to be construed as limited to the particular form shown.

As also used herein, the term "aryl" signifies mononuclear aromatic hydrocarbon groups such as phenyl, tolyl, etc. which can be unsubstituted or substituted in one or more positions with a lower alkylenedioxy, a halogen, a nitro, a lower alkyl or a lower alkoxy substituent, and polynuclear aryl groups such as naphthyl, anthryl, phenanthryl, azulyl, etc., which can be substituted with one or more of the aforementioned gorups. The preferred aryl groups are the substituted and unsubstituted mononuclear aryl groups, particularly phenyl. The term "aryl lower alkyl" comprehends groups wherein aryl and lower alkyl are as defined above, particularly benzyl.

As still further used herein, the term "carboxy protected with a group convertible thereto by hydrolysis" comprehends any conventional organic acid protecting group which can be removed by hydrolysis. The preferred organic acid protecting groups are the esters. Any conventional ester that can be hydrolyzed to yield the acid can be utilized as the protecting group. Exemplary esters useful for this purpose are the lower alkyl esters, particularly methyl and ethyl esters, the aryl esters, particularly phenyl ester and the aryl lower alkyl esters, particularly benzyl ester.

As used herein, the term "hydrolyzable ester or ether group" designates any ester or ether which can be hydrolyzed to yield the hydroxy group. Exemplary ester groups useful for this purpose are those in which the acyl moiety is derived from a lower alkanoic, an aryl lower alkanoic, phosphoric, carbonic or a lower alkane dicarboxylic acid. Among the acids which can be utilized to form such ester groups are the acid anhydrides and the acid halides, preferably chlorides or bromides, with the lower alkanoic acid anhydrides, e.g., acetic anhydride and caproic anhydride, the aryl lower alkanoic acid anhydrides, e.g., benzoic acid anhydrides, lower alkane dicarboxylic acid anhydrides, e.g., succinic anhydride, and chloroformates, e.g., trichloroethylchloroformate, being preferred. A suitable ether protecting group is, for example, the tetrahydropyranyl ether or 4-methoxy-5,6-dihydro-2H-pyranyl ether. Others are arylmethyl ethers such as benzyl, benzyhydryl, or trityl ethers or alpha-lower alkoxy lower alkyl ethers, for example, methoxymethyl or allylic ethers, or trialkyl silyl ethers such as trimethyl silyl ether or dimethyl tert-butyl silyl ethers.

The compounds of formula I wherein $R_2$ and $R_3$ form an oxo group, i.e., the compounds of the formula:

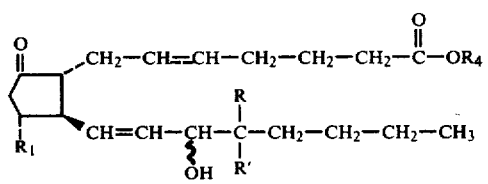

wherein $R_4$, $R_1$, $R$ and $R'$ are as above; and the dotted bond can be optionally hydrogenated;
are useful in the same manner as prostaglandin $E_2$. The compounds of formula I-C are especially valuable for preventing hyperacidity in the stomach, as antiulcerogenic and for broncho-dilation and lowering blood pressure. On the other hand, the compounds of formula I where $R_2$ is hydroxy and $R_3$ is hydrogen, i.e. the compounds of the formula:

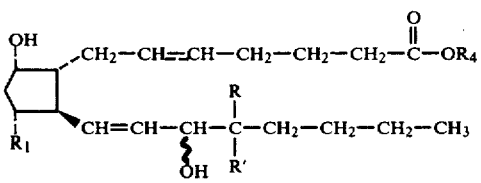

wherein $R_4$, $R_1$, $R$ and $R'$ are as above and the dotted bond can be optionally hydrogenated;
are useful in the same manner as prostaglandin $F_2\alpha$.

The prostaglandins $E_1$, $E_2$ and $F_2\alpha$ have the ability to modify the activity of the alimentary and reproductive smooth muscles to block mucous and enzyme secretions by the stomach, to stimulate the synthesis of adrenal corticoids, to modify blood pressure and liplysis. Since the compounds of formulae I-C, and I-D have prostaglandin $E_1$, $E_2$ and $F_2$ activity, the compounds of formulae I-C and I-D also possess these valuable properties. Furthermore, the compounds of formula I-C and I-D are active in the same manner as these prostaglandins in inducing labor and pregnancy in females and for therapeuticaly terminating pregnancy. The compounds of formula I-C are useful in the same manner as the prostaglandin $E_2$ in that they lower blood pressure and inhibit blood platelet aggregation. On the other hand, the compounds of formula I-D are blood pressure raising agents in the same manner as prostaglandin $F_2\alpha$.

That the compounds of formula I-C are effective anti-ulcerogenic compounds can be seen by the fact that the $ED_{50}$ of a compound such as 7-[3 alpha methyl-5-oxo-2-beta-(3 alpha-hydroxy-4-trifluoromethyl-4-methyl-1-trans-octenyl)-1-alpha-cyclopentyl]-cis-5-heptenoic acid is 0.47 i.p. and 0.0001 p.o. when administered to rats by the following test:

Rats were fasted 16 hours prior to the subcutaneous administration of Indomethacin at 100 mg/kg. Simultaneously with the Indomethacin dose, the test compounds were administered intraperitoneally at three dose levels and dosed orally at six dose lovels. These doses of the test compounds were repeated every thirty minutes for six hours (12 doses). After six hours, the animals were killed and the stomachs were examined for ulceration or hemmorrhage. Protection from incidence of ulceration was used to determine activity. Five mice were used per dose level $ED_{50}$ values were calculated.

The compounds of formula I can be used by the pharmaceutical and veterinary arts in a variety of pharmaceutical or veterinary preparations. In these preparations, the new compounds are administerable in the form of tablets, pills, powders, capsules, injectables, solutions, suppositories, emulsions, dispersions, feed pre-mixes and in other suitable forms. The pharmacuetical or veterinary preparations which contain the compound of formula I are conveniently admixed with a non-toxic pharmaceutical organic carrier or a non-toxic pharmaceutical inorganic carrier. Typical of pharmaceutically acceptable carriers are, for example, water, gelatin, lactose, starches, magnesium stearate, talc, vegetable oils, polyalkylene glycols, petroleum jelly and other conventionally employed pharmaceutically acceptable carriers. The pharmaceutical preparations may also contain non-toxic auxiliary substances such as emulsifying, preserving and wetting agents and the like, as for example, sorbitan monolaurate, triethanol amine oleate, polyoxyethylene sorbitan, dioctyl sodium sulfosuccinate and the like.

The daily dose administered for the compounds will of course vary with the particular novel compounds employed because of the very potency of the compounds, the chosen route of administration and the size of the recipient. The dosage administered is not subject to definite bounds but it will usually be in effective amounts of the pharmacologically function of the prostaglandin. Representative of a typical method for administering the prostaglandin compounds of formula I is by the injectable type administraiton route. By this route, a sterile solution containing the prostaglandin of formula I can be administered intravenously at the rate of 0.01 microgram to 0.15 microgram per day per kilogram of body weight. The compound to be administered by the injectable route is in a form suitable for injection such as mixed with a sterile aqueous solution having incorporated therein an agent that delays adsorption such as aluminium monosterate and the like.

For administering the compounds of formula I to domestic animals or laboratory animals, the compounds are prepared in the form of a food pre-mix such as mixing with dried fish meal, oatmeal and the like and the prepared pre-mix is added to a regular feed thereby administering the compound to the domestic or laboratory animal in the form of a feed.

Depending upon the particular form of the compound of formula I desired, the compound of formula II which is utilized as a starting material can be either a racemate or can be in the form of its optical antipodes.

In preparing the compound of formula I, the compound of formula II is converted to a compound of the formula:

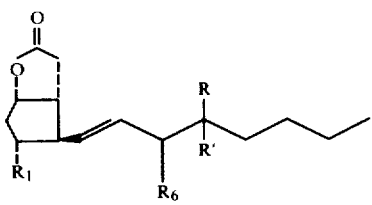

III wherein R, R₁ and R' are as above; and R₆ is hydroxy protected with a hydrolyzable ether or ester group.

In preparing the compound of formula III, the compound of formula II is first converted to a compound of the formula:

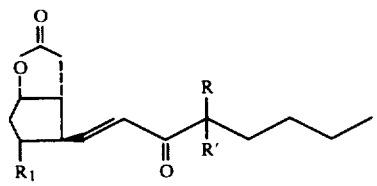

IV wherein R, R₁ and R' are as above;
by reaction with either a phosphorane of the formula:

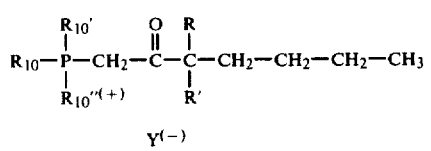

V-A wherein R, and R' are as above, R₁₀, R₁₀' and R₁₀" are aryl or di(lower alkylamino); and Y⁽⁻⁾ is halogen
or a phosphonate of the formula:

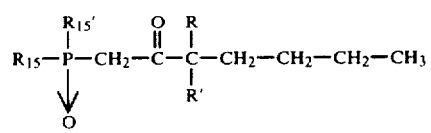

V-B wherein R and R' are as above; and R₁₅ and R₁₅' are aryl, aryloxy or lower alkoxy.

The compound of formula IV is next reduced to a compound of the formula:

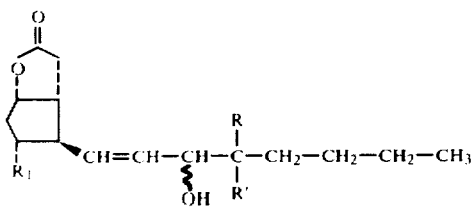

VI wherein R₁, R and R' are as above;

and the free hydroxy group is etherified or esterified to form the compound of formula III.

The reaction of the compound of formula II with the phosphonium salt of formula V-A to produce a compound of formula IV is carried out via a Wittig reaction. Any of the conditions conventional in Wittig reactions can be utilized in carrying out this reaction.

The reaction of the compound of formula II with the phosphonate of formula V-B to produce a compound of formula IV is carried out via a Horner reaction. Any of the conditions conventional in Horner type reactions can be utilized in carrying out this reaction.

The compound of formula VI can be obtained by treating the compound of formula IV with a reducing agent. In carrying out this reaction, any conventional reducing agent which will selectively reduce a keto-group to a hydroxy group can be utilized. Preferred reducing agents are the hydrides, particularly the aluminum hydrides, such as the alkali metal aluminum hydrides and the borohydrides, such as the zinc borohydride or the alkali metal borohydrides, with sodium borohydride being quite particularly preferred. In carrying out this reaction, temperature and pressure are not critical, and the reaction can be carried out at room temperature and atmospheric pressure or at elevated or reduced temperatures and pressures. Generally, it is preferred to carry out this reaction at a temperature of from −30° C. to this reflux temperature of the reaction mixture. This reduction reaction can be carried out in the presence of an inert organic solvent. Any conventional inert organic solvent can be utilized in carrying out this reaction, such as the conventional, inert organic solents hereinbefore mentioned. Among the preferred solvents are methanol, dimethoxy ethylene glycol and the ethers, such as tetrahydrofuran, diethyl ether and dioxane.

The compound of formula VI may be separated into its two isomers by conventional means to produce one isomer of the formula:

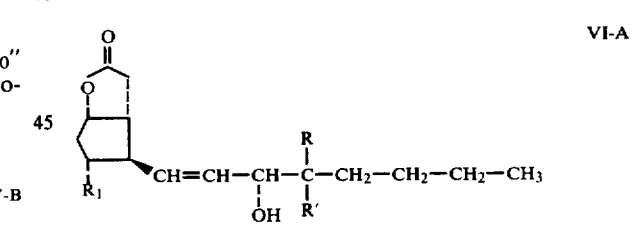

VI-A wherein R₁, R and R' are as above,
and the other isomer of the formula:

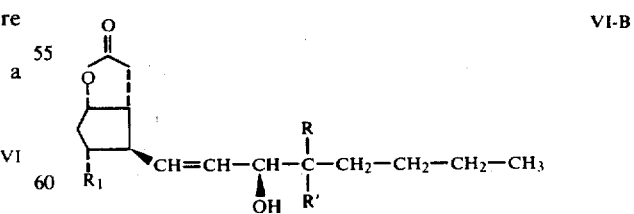

VI-B wherein R₁, R' and R are as above.

Any conventional means of separation such as column chromatography, vapor phase chromatography, etc., can be utiized to carry out this separation. Either of these isomers can be utilized in accordance with this reaction to produce the compound of formula I. The configuration of the hydroxy group on the octenyl side chain will be carried through the process of this invention so that the hydroxy group on the octenyl side chain in the compound of formula I will have the same configuration as it has in the starting material of formula VI-A or VI-B.

The compound of formulae VI, VI-A and VI-B can be converted to a compound of the formula III by esterifying or etherifying the free hydroxy group with a hydroxylyzable ether or ester protecting group. This esterification or etherification can be carried out by conventional esterification procedures. Among the preferred hydrolyzable ester groups are lower alkanoyloxy with acetoxy being especially preferred. Among the preferred hydrolyzable ether groups are included tetrahydropyranyl.

The compound of formula III is converted to a compound of formula I

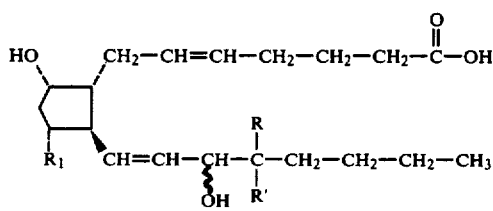    I-D via the following intermediates

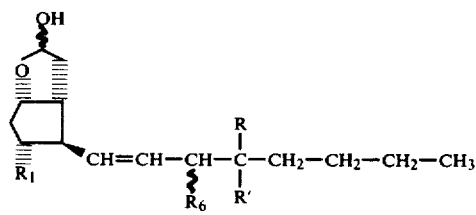    X wherein R, $R_1$, R' and $R_6$ are as above;

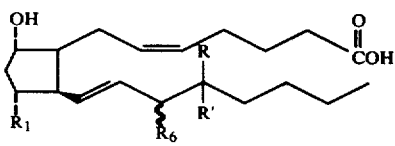    XI $R_1$, R, R' and $R_6$ are as above.

The compound of formula III is converted to the compound of formula X by treating the compound of formula III with a reducing agent. In carrying out this reaction, any conventional reducing agent which will selectively reduce a keto-group to a hydroxy-group can be utilized. Among the reducing agents are included the hydrides, as well as alkali metal borohydrides, with di-isobutyl aluminum hydride being particularly preferred. Also, this reaction can be carried out utilizing di-(branched chain lower alkyl)boranes such as bis(3-methyl-2-butyl)borane. In carrying out this reaction, temperature and pressure are not critical and the reaction can be carried out at room temperature and atmospheric pressure or elevated or reduced temperatures and pressures. Generally, it is preferred to carry out this reaction at a temperatures of from −70° C. to room temperature (30° C.). This reduction reaction can be carried out in the presence of an inert organic solent. Any conventional inert organic solvents can be utilized in carrying out this reaction. Among the preferred solvents are dimethoxy ethylene glycol, and the ethers such as tetrahydrofuran, diethyl ether and dioxane.

The compound of formula XI is obtained from the compound of formula X by reacting the compound of formula X with phosphonium salts of the formula:

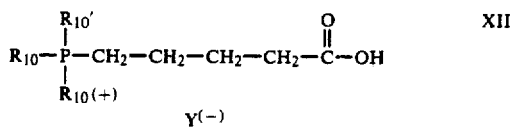    XII wherein $R_{10}$, $R_{10}'$, $R_{10}''$ is as above; and Y is halogen.

In accordance with this invention, it is found that the compound of formula X will react with the compound of formula XII to produce a compound of the formula XI with a predominantly cis double bond at the 5 position of the acid chain in a solvent medium containing hexamethylphosphoramide utilizing sodium bis-trimethylsilylamide as a base. If solvents other than hexamethylphosphoramide or bases other than sodium bis-trimethylsilylamide are utilized, the compound of formula XI may form in poorer yields. However, conventional inert organic solvents may be mixed with the hexamethylphosphoraide to form the solvent medium in accordance with this invention. If other solvents are utilized, these solvents can be conventional inert organic solvents. On the other hand, the solvent system can contain only the hexamethylphosphoramide. Therefore, this reaction is carried out utilizing hexamethylphosphoramide as the solvent and sodium bis-trimethylsilyl-amide as the base. In carrying out this reaction, temperature and pressure are not critical and this reaction can be carried out at room temperature and pressure. However, if desired, higher or lower temperatures can be utilized. Generally, it is preferred to carry out this reaction at a temperature of from 0° to 50° C.

The compound of formula XI is converted to the compound of formula I-D by aqueous acid hydrolysis where the hydroxy group is protected via an ether linkage. Any conventional method of ether hydrolysis can be utilized. Among the preferred methods of ether hydrolysis is by treating the compound of formula XI with an aqueous inorganic acid. On the other hand, where $R_6$ forms an ester linkage, the hydroxy group can be regenerated by treatment with a base in an aqueous medium. Any conventional method of ester hydrolysis can be utilized in this conversion. Among the preferred bases is aqueous sodium hydroxide.

On the other hand, the compound of formula XI above can be converted to a compound of the formula:

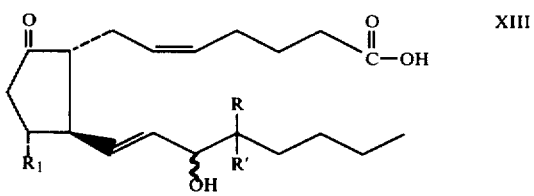    XIII wherein $R_1$, R and R' are as above;
via an intermediate of the formula:

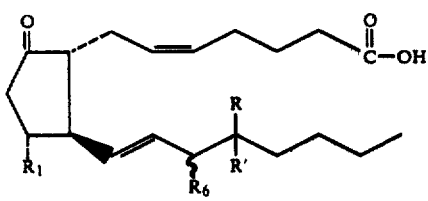

wherein $R_6$, $R$, $R_1$ and $R'$ are as above.

The compound of formula XI is converted to a compound of formula XIV by treating the compound of formula XI with an oxidizing agent. Any conventional oxidizing agent which will convert a hydroxy group to an oxo group can be utilized in carrying out this reaction. Among the preferred oxidizing agents are chromate oxidizing agents such as chromium trioxide. Any of the conditions conventional in utilizing these oxidizing agents can be utilized to carry out this reaction. The compound of formula XIV is converted to the compound of formula XIII by hydrolysis in the same manner as described in connection with the hydrolysis of a compound of formula XI.

The compounds of formula XI, XIII, XIV and I-D can be converted to a compound of the formula:

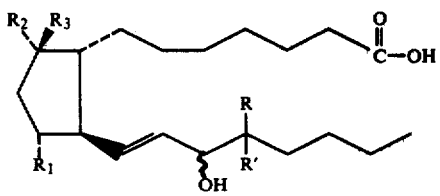

wherein $R_1$, $R_2$, $R_3$, $R$ and $R'$ are as above;
by hydrogenation. Any conventional method of hydrogenation such as catalytic hydrogenation can be utilized to carry out this conversion. Among the preferred methods of hydrogenation is by reacting these compounds with hydrogen in the presence of a noble metal catalyst such as platinum or palladium under conditions conventional for such hydrogenation. After hydrogenation, the protecting group on the hydrogenated compounds of formula XI or XIV can be removed by hydrolysis.

The compounds of formulae I-D, I-E and XIII can be converted to a compound of the formula:

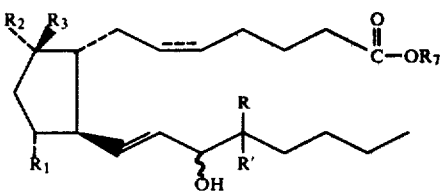

wherein $R_1$, $R_2$, $R_3$, $R$ and $R'$ are as above; $R_7$ is lower alkyl; and the dotted bond can be optionally hydrogenated;
by esterification with diazomethane or a reactive derivative of a lower alkanol such as a lower alkyl halide. Any conventional conditions utilized in esterification can be utilized in forming the compound of formula I-F from the compounds of formulae I-D, I-E and XIII. On the other hand, the compound of formula I-F can be formed from the compounds of the formulae XI or XIV where $R_6$ is hydroxy protected with a hydroxyzable ether group by esterification as described above to form a compound of the formula:

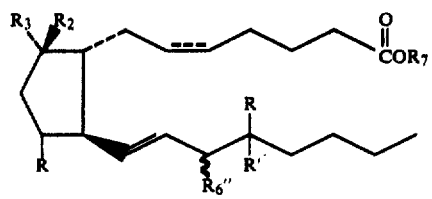

wherein $R_1$, $R'$, $R_2$, $R_3$, $R$ and $R_7$ are as above; and $R_6''$ is hydroxy protected with a hydrolyzable ether group and the dotted bond can be optionally hydrogenated.

The compound of formula I-G is converted to the compound of formula I-F by conventional ether hydrolysis as described above.

The compounds of formula VB other than compounds where when $R'$ is hydrogen, $R$ is trifluoromethyl are prepared by reacting a lithium salt of the formula:

wherein $R_{15}$ is as above;
with a compound of the formula:

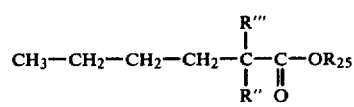

wherein $R_{25}$ is lower alkyl; $R''$ is fluoro, lower alkyl or trifluromethyl; $R'''$ is hydrogen, fluorine or lower alkyl with the proviso that when $R''$ is trifluoromethyl, $R'''$ is other than hydrogen.

Any of the conditions conventional for reacting a lithium salt with an ester to form an addition product can be used in this reaction.

In accordance with this invention, the compound of formula V-B can be produced from a compound of the formula:

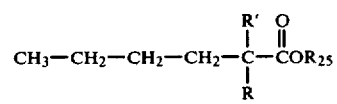

wherein $R$, $R'$ and $R_{25}$ are as above
via the following intermediates

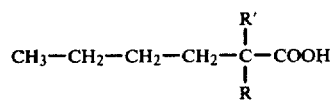

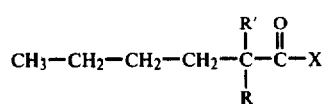

-continued

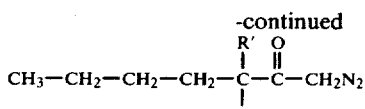

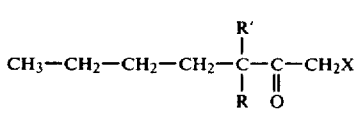

wherein R', R are as above; and X is halogen.

The compound of formula XIX-A is converted to the compound of formula XXII by acid hydrolysis. Any conventional method of acid hydrolysis can be utilized to affect this conversion. Generally this hydrolysis is carried out at from 20° C. to 120° C. in the presence of an aqueous mineral acid such as sulfuric acid. The compound of formula XXII is converted to the compound of formula XXIII by treating with a halogenating agent. Any conventional halogenating agent can be utilized to affect this conversion. Among the preferred halogenating agents are included: oxalyl chloride and thionyl chloride, phosphorous pentachloride. Any of the conditions conventional in utilizing these halogenating agents can be utilized in carrying out this conversion.

The compound of formula XXIII can be converted to the compound of formula XXIV by reaction with diazomethane under conditions conventional in reacting an acid halide with diazomethane. The compound of formula XXIV is converted to the compound of formula XXV by treatment with a gaseous hydrohalide acid such as gaseous hydrogen bromide under conditions conventional for converting a diazo compound to a halide. The compound of formula XXV is converted to a compound of formula V-B by reaction with a tri(-lower alkyl) phosphite under conditions conventional for this reaction. The compound of formula XXV can also be converted to the compound of formula V-A by reaction with a tri [aryl or di(lower alkyl)amino]phosphine under conditions conventional for this reaction.

The compound of formula XIX-A where R is $CF_3$, i.e. a compound of the formula

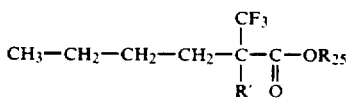

where R' and $R_{25}$ are as above
can be prepared from a compound of the formula:

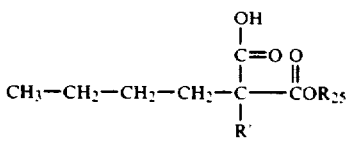

where R' and $R_{25}$ are as above
by reacting the compound of formula XXVI with sulfur tetrafluoride. In carrying out this reaction, the sulfur tetrafluoride is reacted with the compound of formula XXVI in a closed container at a temperature of from 20° to 85° C. Generally from about 1 to 4 moles of the sulfur tetrafluoride is present per mole compound of formula XXVI. Amounts of the sulfur tetrafluoride greater than four moles per mole of the compound of formula XXVI may be present in the reaction medium. If desired, acid catalysts and/or a solvent may be present in the reaction medium. Any conventional inert organic solvent, preferably the halogenated hydrocarbon solvents such as methylene chloride may, if desired, be present in the reaction medium. If desired, any conventional acid catalyst such as hydrofluoric acid, boron trifluoride, etc. can be added to in the reaction medium. On the other hand, no solvent and/or acid catalyst need be added to the reaction medium.

Of the compounds of formula XIX-B, the compounds where R' is a lower alkyl and fluoro are new compounds.

The compound of formula V-A other than those compounds where when R' is hydrogen, R is trifluoromethyl, can also be prepared by reacting a compound of the formula XXIII with a compound of the formula

wherein $R_{10}$, $R_{10}'$ and $R_{10}''$ are as above
utilizing conditions conventional for forming Wittig reactants.

The compound of formula V-B can also be prepared by reacting the compound of formula XXIII with a compound of the formula

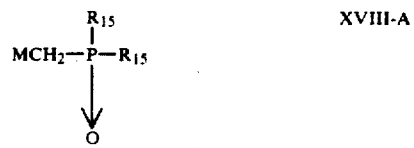

where M is lithium and copper.

This reaction is carried out utilizing any of the conditions conventional for reacting a metal salt with an acid halide to form an addition product.

In accordance with this invention, a new means is provided for producing the compound of the formula II where $R_1$ is methyl or $-COOR_1'$, in optically active form, i.e. an optically active compound of the formula:

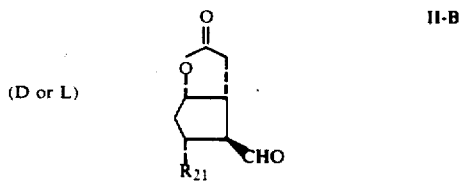

wherein $R_{21}$ is methyl, $-COOR'$, or $CH_2OR_1'$; and $R_1'$ is as above;
from a racemate of the formula

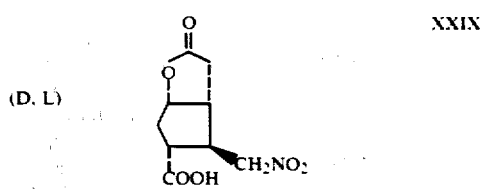

In accordance with this aspect of this invention, the racemate of formula XXIX is treated with a suitable optically active resolving agent of the formula

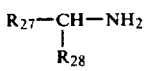 XXX wherein R$_{27}$ is

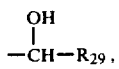

tolyl, naphthyl, phenyl or naphthyl or phenyl substituted with nitro or halo; R$_{29}$ is tolyl, naphthyl, phenyl or napthyl or phenyl substituted with nitro or halo, R$_{28}$ is —CH$_2$R$_{31}$; and R$_{31}$ is hydrogen, lower alkyl, hydroxy or lower alkoxy to produce an optically active salt of the formula:

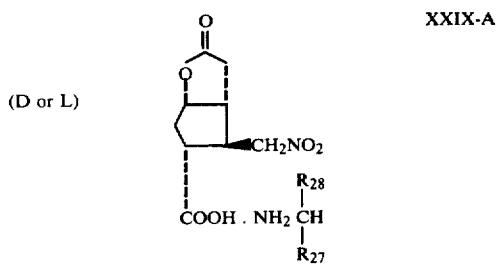 XXIX-A wherein R$_{27}$ and R$_{28}$ are as above;
The salt is then neutralized to produce the desired optically active isomer of formula:

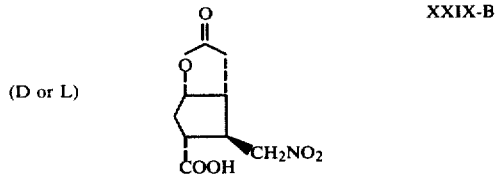 XXIX-B

In accordance with this invention, the racemate of formula XXIX is treated with the suitable optically active resolving agent of formula XXX in its desired optically active form. The optically active form of the compound of formula XXX will determine which optically active compound of formula XXIX-A is isolated Where R$_{29}$ and R$_{27}$ is naphthyl or phenyl, these groups can be unsubstituted. On the other hand, the naphthyl and phenyl group can be substituted with a halo or nitro substituent. The substituents can be in either the ortho, meta or para positions. Among the preferred optically active resolving agents of formula XXX are included the optically active forms of alpha-methyl benzyl amine, alpha-methyl p-nitro benzylamine, alpha-(1-naphthyl)ethyl amine, or 1-phenyl-2-amino-3-substituted-1-propanol where the 3-substituent is substituted with a lower alkyl, hydroxy, or lower alkoxy radical.

In preparing the optically active salt of the formula XXIX-A, the racemate is treated with the suitable optically active form of the compound of formula XXX. This treatment takes place in an inert organic solvent medium. Any conventional inert organic solvent medium can be utilized for this salt formation. Among the preferred organic solvents are lower alkanols such as ethanol, acetonitrile, lower alkyl ketones such as acetone, methyl ethyl ketone, methyl isobutyl ketone, dioxane, formamide. In carrying out this treatment, temperature and pressure are not critical, and the treatment can be carried out at room temperature and atmospheric pressure. On the other hand, higher temperatures can be utilized. Generally, it is preferred to carry out the formation of the salt at a temperature of from 20° C. to 85° C. Generally the use of higher temperatures in the salt formation is an aid to the later crystallization of the salt of formula XXIX-A. In this manner, a saturated solution of the salt of formula XXIX-A can be formed at a higher temperature. Upon lowering the temperature to room temperature, the salt of formula XXIX-A can crystalize out of solution. On the other hand, any conventional method of crystallization can be utilized to obtain the desired optically active salt of formula XXIX-A as a crystalline material.

The optically active salt of formula XXIX-A can be converted to the optically active isomer of formula XXIX-B by neutralization. Any conventional method of neutralization such as treating the compound of formula XXIX-A with an inorganic acid can be utilized to produce the compound of formula XXIX-B.

The compound of formula XXIX or its optically active antipodes can be converted to the compound of formula II-B where R$_{21}$ is —COOH or its optically active antipodes via the following intermediate:

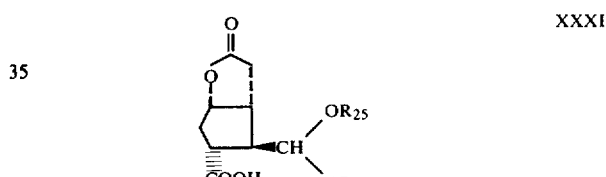 XXXI where R$_{25}$ is as above
or its optically active antipodes.

The compound of formula XXIX is converted to the compound of formula XXXI by first forming its aci-nitro salt by treatment with an alkali metal lower alkoxide, preferably sodium methoxide. In carrying out this reaction, temperatures of from −50° to 35° C. are utilized, with temperatures at −35° C. to −20° C. being preferred. This reaction can be carried out in a lower alkanol. The aci-nitro salt derived from the compound of formula XXIX is converted to the compound of formula XXXI by treatment with sulfuric acid in a lower alkanol. In carrying out this reaction, temperatures of from −50° C. to 35° C. are utilized. The compound of formula XXXI is converted to the compound of formula II-B where R$_{21}$ is —COOH by aqueous acid hydrolysis. Any conventional method of aqueous acid hydrolysis can be utilized to affect this conversion. If desired, the compound of formula II-B where R$_{21}$ is —COOH can be esterified by conventional procedures.

On the other hand, the compounds of the formula XXIX-B, either as racemates or as an optically active isomer, can be converted to the compound of II-B where R$_{21}$ is —CH$_3$, in its optically active form or as a racemate via the following intermediates:

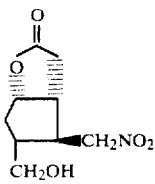
XXXII; and

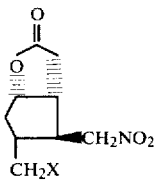
XXXIII wherein X is halogen.

The compounds of formula XXIX-B either as racemates or in its optically active form, can be converted to the compound of formula XXXII by treatment with a borane reducing agent. Generally for safety purposes, the borane is in the form of a complex with methylsulfide or tetrahydrofuran. In carrying out this reaction, any of the conditions conventional in borane reduction can be utilized. This borane reduction produces the compound of formula XXXII. The compound of formula XXXII is converted to the compound of formula XXXIII by treatment with a halogenating agent. Any conventional method of halogenating can be utilized to affect the conversion of the compound of the formula XXXII to the compound of the formula XXXIII. In accordance with a preferred embodiment of this invention, the compound of formula XXXII is treated with a halogen such as iodine, or bromine in the presence of triphenylphosphine. the compound of formula XXXIII is converted to the compound of the formula II-B where $R_{21}$ is —$CH_3$ by treating the compound of formula XXIII with a borohydride reducing agent such as sodium cyanoborohydride. Any of the conditions conventional in utilizing this borohydride reducing agent can be utilized to affect this conversion.

The compound of formula XXXII is the compound of formula II-B where $R_{21}$ is —$CH_2OH$. This compound can be converted to the compound of III-B where $R_{21}$ is —$CH_2OR_7$ by etherification in the conventional manner with a reactive derivative of a lower alkanol acid. The compound of formula II-B where $R_{21}$ is

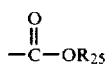

can be prepared from the compound of formula II-B where $R_{21}$ is —COOH by esterification.

In accordance with another aspect of this invention, the compound of formula V-A and V-B can be produced in optically active form through the use of the compound of formula XXIII with an asymmetric carbon atom, i.e. a compound of the formula:

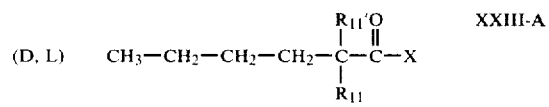
XXIII-A wherein $R_{11}$ is fluoro, lower alkyl or trifluoromethyl; $R_{11}'$ is hydrogen, fluoro, or lower alkyl; with the proviso that $R_{11}$ and $R_{11}'$ are not the same substituent or n-butyl.

In this procedure, the racemic compound of formula XXIII-A is reacted with the optically active isomer of the formula XXX to form the optically active amide of the formula

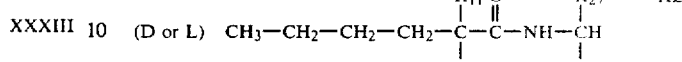
XL wherein $R_{11}$ and $R_{11}'$ are as above and $R_{27}$ and $R_{28}$ are as above;

as a diasteriomeric mixture. Any conventional method of reacting an amine with an acid halide can be used to form the compound of formula XL.

Among the preferred compounds of formula XXX for use in the resolution are α-methyl-p-nitro benzyl amine or 1-phenyl-2-amino-b 3-unsubstituted or substituted-1-propanol in their optically active form which produce amides of the compound of formula XL, i.e.

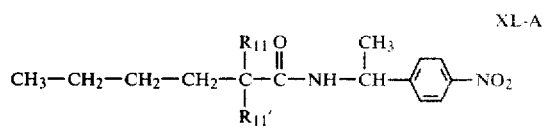
XL-A wherein $R_{11}$ and $R_{11}'$ are as above or

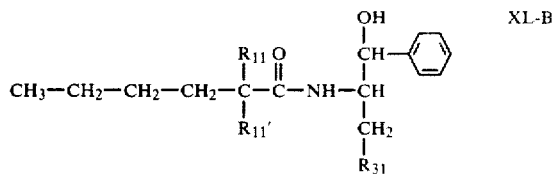
XL-B wherein $R_{11}$ and $R_{11}'$ are as above, and $R_{31}$ is hydrogen, hydroxy, lower alkyl or lower alkoxy.

The diastereoisomers of formula XL can be separated by conventional techniques such as chromotography. Generally, it is preferred to utilize high pressure chromotography to carry out this separation.

The optically active form of the compound of formula XL can be converted to the optically active form of the compound of formula XXII by treating the optically active form of the compound of formula XL with a dilute inorganic mineral acid such as from 1 to 10 normal aqueous hydrochloric acid.

In accordance with a preferred embodiment, the compound of formula XL-A in its optically active form is converted to the optically active compound of formula XXII by first reducing the nitro group to an amino group to produce a compound of the formula (D or L)
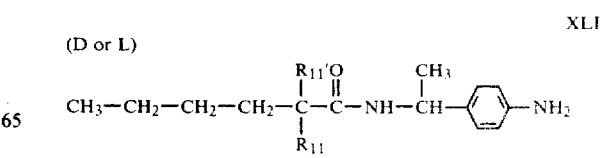
XLI wherein $R_{11}$ and $R_{11}'$ are as above.

The optically active form of the compound of formula XL-A is converted to the compound of XLI by hydrogenation. Any conventional method of catalytic hydrogenation utilizing conventional hydrogenation catalysts such as palladium can be utilized to affect this conversion. The optically active form of the compound of formula XLI is converted to the optically active form of the compound of formula XXII by acid cleavage. Any conventional method of acid hydrolysis can be utilized to carry out this reaction.

The use of the aforementioned means has been found to produce the optical isomers of the compound of formula XXII and XXIII in good yields. The compound of formula XXII and XXIII are very difficult compounds to resolve in view of the fact that they contain either a secondary or tertiary fluoro or trifluoromethyl. This fluorine or trifluoromethyl group is very reactive and upon acid treatment will form side products such as by elimination of a hydrogen and fluorine to form a double bond and by the formation of a hydroxy group rather than a fluoro substituent. It has been found that the use of the aforementioned means provides an efficient method for resolving a compound of formula XXII or XXIII without the danger of forming side products. The reduction of the nitro group at the para position in the compound of formula XL-A to an amino group in the compound of formula XLI allows the subsequent cleavage to take place without the formation of undesirable side products. Therefore, the two aforementioned means allow the compound of formula XXII and XXIII to be resolved in high yields without the formation of undesirable by-products.

In accordance with a preferred embodiment of this invention, the optical isomer of 1-phenyl-2-amino-3-methoxy propanol is preferably utilized when $R_{11}'$ is lower alkyl and $R_{11}$ is fluorine or trifluoromethyl and α-methyl p-nitrobenzylamine is utilized when $R_{11}'$ is hydrogen and $R_{11}$ is fluorine or trifluoromethyl.

The optical antipodes of the formula XXII and XXIII can be converted to form the optically active antipode of formulae V-A or V-B. This optically active center will be carried through the conversion of the compound of formula XXII and XXIII to the compounds of formulae V-A or V-B and on to the prostaglandin compounds of formula I which are optically active about the C-16 position.

EXAMPLE 1

3,3aR,4,5,6,6aS-Hexahydro-4R-nitromethyl-5R-carboxy-2H-cyclopenta[b]furan-2-one

A solution of 62 g (0.27 mol) of racemic 3,3abeta,4,5,6,6abeta-hexahydro-4beta-nitromethyl-5alpha-carboxy-2H-cyclopenta[b]furan-2-one in 3.0 l of acetonitrile was warmed to 65° C. and mixed with a solution of 27 g (0.16 mol) of R-(+)-α-methyl-p-nitrobenzyl amine in 0.7 l of acetonitrile. The solution was allowed to cool to 25° C. and after 5 hr. at this temperature, the crystal crop was filtered. Three recrystallizations from acetonitrile yielded 21.8 g (41%) of amine salt; mp 181°–2°dec, $[\alpha]_D - 36.3°$ (1% in DMSO). Evaporation of the combined mother liquors from the recrystallizations gave 24 g of crude salt which gave an additional 12.9 g of pure material after four recrystallizations from acetonitrile. The combined salts (34.7 g) were mixed with saturated NaCl solution (100 ml), 4 NHCl (50 ml) and ethyl acetate (300 ml). This mixture was filtered, and the ethyl acetate layer separated and evaporated to dryness to give 20.5 g (100%) of 3,3aR,4,5,6,6aS-hexahydro-4R-nitromethyl-5R-carboxy-2H-cyclopenta[b]furan-2-one, mp. 103°–105° C., $[\alpha]_D - 65.4°$ (1% in CH₃CN) after recrystallization from ethyl acetate/hexane.

Calc. for $C_9H_{11}NO_6$: C 47.19, H 4.84, N 6.11; Found: C 47.16, H 5.04, N 6.18.

EXAMPLE 2

3,3aS,4,5,6,6aR-Hexahydro-4S-nitromethyl-5S-carboxy-2H-cyclopenta[b]furan-2-one

By the procedure of Example 1, racemic 3,3abeta,4,5,6,6abeta-hexahydro-4-beta-nitromethyl-5alpha carboxy-2H-cyclopenta[b]furan-2-one was resolved with S-(−)-α-methyl-p-nitrobenzyl amine to give 3,3aS,4,5,6,6aR-hexahydro-4S-nitromethyl-5S-carboxy-2H-cyclopenta[b]furan-2-one; mp. 103°–105°, $[\alpha]_D + 65.2°$ (1% in CH₃CN).

Calc. for $C_9H_{11}NO_6$: C 47.19, H 4.84, N 6.11; Found: C 47.35, H 5.05, N 6.18.

EXAMPLE 3

3,3aR,4,5,6,6aS-Hexahydro-4S-nitromethyl-5R-hydroxymethyl-2H-cyclopenta[b]furan-2-one Borane-methyl sulfide complex (25 ml, 0.25 mol) was added dropwise over a 30 minute period to an ice cold solution of 3,3aR,4,5,6,6aS-hexahydro-4R-nitromethyl-5R-carboxy-2H-cyclopenta[b]furan-2-one (45.8 g, 0.2 mol) in ethyl acetate (1 l). The ice bath was removed and the reaction stirred at RT for 20 hr. After this period, methanol (300 ml) was carefully added and the mixture was evaporated to constant weight at reduced pressure. The crude material was taken-up in 400 ml of methanol followed by evaporation to constant wt. to give 43 g (100%) of 3,3aR,4,5,6,6aS-hexahydro-4S-nitromethyl-5R-hydroxymethyl-2H-cyclopenta[b]furan-2-one. An analytically pure sample was prepared by column chromatography over silica gel using 2:3 ethyl acetate/benzene as the eluent to give the pure alcohol as a colorless oil, $[\alpha]_D - 31.9°$ (1% in dioxane).

Calc. for $C_9H_{13}NO_5$: C 50.23, H 6.09, N 6.51; Found: C 50.51, H 6.08, N 6.41.

EXAMPLE 4

3,3aR,4,5,6,6aS-Hexahydro-4S-nitromethyl-5R-methyl-2H-cyclopenta[b]furan-2-one

Iodine (81.3 g, 0.32 mol) was added in 4–5 g portions over a 20 minute period to a stirred solution of 3,3aR,4,5,6,6aS-hexahydro-4S-nitromethyl-5R-hydroxymethyl-2H-cyclopenta[b]furan-2-one (66.3 g, 0.308 mol.) and triphenylphosphine (83.8 g, 0.32 mol.) in hexamethylphosphoramide (1 l) at RT. Thin layer analysis indicated complete conversion to 3,3aR,4,5,6,6aS-hexahydro-4S-nitromethyl-5R-iodomethyl-2H-cyclopenta[b]furan-2-one within 5 hr. The ppt. of triphenylphosphine oxide was filtered and the filtrate was mixed with sodium cyanoborohydride (50 g, 0.8 mol.) and warmed to 70° C. for 18 hr. The reaction mixture was poured into a separatory funnel containing sat. NaCl solution (1 l.), water (1 l), and ethyl acetate (2 l). The organic phase was separated, dried (MgSO₄) and evaporated to constant wt. at reduced pressure. The majority of the HMPA was removed from the residual material by a bulb to bulb distillation at 70°–80°/0.1 mm and the residue purified by column chromatography over silica gel using 0–10% ethyl acetate/benzene as the eluent to give 51.5 g (84%) of 3,3aR,4,5,6,6aS-hexahydro-4S- nitromethyl-5R-methyl-2H-cyclopenta[b]furan-2-one as a colorless oil; $[\alpha]_D - 48.87°$ (1% in $CH_3CN$).

Calc. for $C_9H_{13}NO_4$: C 54.27, H 6.58, N 7.03; Found: C 54.47, H 6.57, N 6.98.

EXAMPLE 5

3,3aR,4,5,6,6aS-Hexahydro-4S-dimethoxymethyl-5R-methyl-2H-cyclopenta[b]furan-2-one A solution of 3,3aR,4,5,6,6aS-hexahydro-4S-nitromethyl-5R-methyl-2H-cyclopenta[b]furan-2-one (13.66 g, 68.8 mmol) in 140 ml (70 mmol) of 0.5 M sodium methoxide/methanol was added dropwise to a rapidly stirred solution of conc. sulfuric acid (165 ml) in methanol (650 ml) at $-40°$ C. The resulting solution was added dropwise, via a double-tipped needle, to a rapidly stirred slurry of potassium bicarbonate (775 g), water (1 l), and ethyl ether (700 ml). This mixture was filtered and the organic layer separated, dried ($Na_2SO_4$) and solvents evaporated at reduced pressure. The residual oil was purified by column chromatography over silica gel using ether as the eluent to give 13.2 g (90%) of 3,3aR,4,5,6,6aS-hexahydro-4S-dimethoxymethyl-5R-methyl-2H-cyclopenta[b]furan-2-one as a colorless oil; $[\alpha]_D - 34.6°$ (1% in $CH_3CN$).

Calc. for $C_{11}H_{18}O_4$: C 61.66, H 8.47; Found: C 61.72, H 8.47.

EXAMPLE 6

3,3aR,4,5,6,6aS-Hexahydro-4S-formyl-5R-methyl-2H-cyclopenta[b]furan-2-one

A mixture of 3,3aR,4,5,6,6aS-hexahydro-4S-dimethoxymethyl-5R-methyl-2H-cyclopenta[b]furan-2-one (15.1 g, 0.07 mol), trifluoroacetic acid (25 ml), water (25 ml) and chloroform (300 ml) was vigorously stirred at RT for 3 hr. The layers were separated and the water layer extracted with $2 \times 50$ ml of $CHCl_3$. The combined organic layers were washed with sat. $NaHCO_3$ solution, dried ($MgSO_4$) and evaporated to constant weight to give 11.3 g (96%) of oily 3,3aR,4,5,6,6aS-Hexahydro-4S-formyl-5R-methyl-2H-cyclopenta[b]furan-2-one, which was not further purified. An analytical sample was prepared by column chromatography over silica gel using ether as the eluent to give 3,3aR,4,5,6,6aS-hexahydro-4S-formyl-5R-methyl-2H-cyclopenta[b]furan-2-one as a colorless oil; $[\alpha]_D - 38.06°$ (1% in $CH_3CN$).

Calc. for $C_9H_{12}O_3$: C 64.27, H 7.19; Found: C 64.06, H 7.38.

EXAMPLE 7

3,3aR,4,5,6,6aS-Hexahydro-4R-(4,4-dimethyl-3-oxo-1-trans-octenyl)-5R-methyl-2H-cyclopenta[b]furan-2-one A solution of 16.5 g (66 mmol) of dimethyl (3,3-dimethyl-2-oxoheptyl) phosphonate in 1,2-dimethoxyethane (50 ml) was added dropwise to a stirred slurry of 3.12 g (65 mmol) of 50% sodium hydride-mineral oil in 1,2-dimethoxyethane (500 ml) under a positive argon atm. at RT. After 2.5 hr., a solution of 3,3aR,4,5,6,6aS-hexahydro-4S-formyl-5R-methyl-2H-cyclopenta[b]furan-2-one in 1,2-dimethoxyethane (100 ml) was added dropwise and the mixture stirred for 4 hr. at RT. After this time, the reaction mixture was placed in a separatory funnel with 100 ml of sat. NaCl soln. and 1 l of ether. The layers were separated and the organic layer washed with $2 \times 50$ ml of sat. NaCl soln., dried ($MgSO_4$) and evaporated to constant weight to give 22.5 g of a dark oil. Purification by column chromatography on silica gel (benzene) gave 11.27 g (63%) of 3,3aR,4,5,6,6aS-hexahydro-4R-(4,4-dimethyl-3-oxo-1-trans-octenyl)-5R-methyl-2H-cyclopenta[b]furan-2-one. Recrystallization from ether gave colorless crystals; mp 59°–61°, $[\alpha]_D + 7.00°$ (1% in $CH_3CN$).

Calc. for $C_{18}H_{28}O_3$: C 73.94, H 9.65; Found: C 73.65; H 9.66.

EXAMPLE 8

3,3aR,4,5,6,6aS-Hexahydro-4R-(4,4-dimethyl-3R-hydroxy-1-trans-octenyl)-5R-methyl-2H-cyclopenta[b]furan-2-one and 3,3aR,4,5,6,6aS-hexahydro-4R-(4,4-dimethyl-3S-hydroxy-1-trans-octenyl)-5R-methyl-2H-cyclopenta[b]furan-2-one A solution of 3,3aR,4,5,6,6aS-hexahydro-4R-(4,4-dimethyl-3-oxo-1-trans-octenyl)-5R-methyl-2H-cyclopenta[b]furan-2-one (2.07 g) in 10 ml of methanol was added to a solution of 0.67 g of sodium borohydride in 25 ml of methanol at $-23°$ C. After 1 hr, the reaction mixture was acidified to pH 5.5 with 1 N $H_2SO_4$. The methanol was removed at reduced pressure and the residue extracted with $3 \times 30$ ml of ether. Evaporation of the ether gave 2.2 g of crude material which was purified by column chromatography over silica gel using 30% ethyl acetate/benzene as the eluent to give 1.3 g of 3,3aR,4,5,6,6aS-hexahydro-4R-(4,4-dimethyl-3R-hydroxy-1-trans-octenyl)-5R-methyl-2H-cyclopenta[b]-furan-2-one as a colorless oil, $[\alpha]_D + 5.62°$ (1% in $CH_3CN$).

Calc. for $C_{18}H_{30}O_3$: C 73.43, H 10.27; Found: C 73.51, H 10.31.

Additionally, there was obtained 0.7 g of 3,3aR,4,5,6,6aS-hexahydro-4R-(4,4-dimethyl-3S-hydroxy-1-trans-octenyl)-5R-methyl-2H-cyclopenta[b]-furan-2-one as a colorless oil; $[\alpha]_D - 30.0°$ (1% in $CH_3CN$).

Calc. for $C_{18}H_{30}O_3$: C 73.43, H 10.27; Found: C 73.23, H 10.30.

EXAMPLE 9

3,3aR,4,5,6,6aS-Hexahydro-4R-[4,4-dimethyl-3R(2-tetrahydropyranyloxy)-1-trans-octenyl]-5R-methyl-2H-cyclopenta[b]furan-2-ol To a solution of 3,3aR,4,5,6,6aS-hexahydro-4R-(4,4-dimethyl-3R-hydroxy-1-trans-octenyl)-5R-methyl-2H-cyclopenta[b]furan-2-one (3.02 g, 10.2 mmol) in methylene chloride (70 ml) was added 1.1 ml of dihydropyran and 1 mg of p-toluenesulfonic acid. After 3 hrs. at RT, several drops of sat. $NaHCO_3$ solution were added and the reaction evaporated to constant wt. at reduced pressure to give 3,3aR,4,5,6,6aS-hexahydro-4R-[4,4-dimethyl-3R-(2-tetrahydropyranyloxy)-1-trans-octenyl]-5R-methyl-2H-cyclopenta[b]furan-2-one. This crude material was then mixed with 250 ml of dry toluene. The flask was sealed under a positive argon atm. and cooled to $-78°$ C. With rapid stirring, 7 ml (10.5 mmol) of 1.5 M di(isobutyl) aluminum hydride/hexane was added dropwise. After 30 min., the reaction mixture was mixed with ether (500 ml), sat. NaCl solution (50 ml) and 2 N HCl (20 ml). The layers were separated and the organic layer dried ($MgSO_4$) and the solvents removed at reduced pressure. The residual oil was purified by column chromatography using 3:7 parts by volume ether/hexane as the eluent to give 3.22 g (83%) of 3,3aR,4,5,6,6aS-hexahydro-4R-[4,4-dimethyl-3R(2-tetrahydropyranyloxy)-1-trans-octenyl]-5R-methyl-2H-cyclopenta[b]furan-2-ol as a colorless oil; $[\alpha]_D + 7.93°$ (1% in $CH_3CN$).

Calc. for $C_{23}H_{40}O_4$: C 72.59, H 10.59; Found: C 72.44; H 10.72.

EXAMPLE 10

Nat-11R,16,16-Trimethyl-15R-(2-tetrahydropyranyloxy)-9S-hydroxy-prosta-cis-5,trans-13-dienoic acid Sodium bis (trimethylsilyl) amide (6.7 g, 36 mmol) was dissolved in 100 ml of HMPA and the resulting solution degassed from a stream of argon. This solution was transferred under a positive argon atm via a double-tipped needle to a slurry of (4-carboxybutyl)triphenylphosphonium bromide [7.96 g (18 mmol) dried at 100°/0.3 mmHg] in 100 ml of HMPA. This mixture was stirred under a positive argon atm until all the solid dissolved and the deep-red color of the Wittig reagent formed. A solution of 3.22 g (8.42 mmol) of 3,3aR,4,5,6-,6aS-hexahydro-4R-[4,4-dimethyl-3R(2-tetrahydropyranyloxy)-1-trans-octenyl]-5R-methyl-2H-cyclopenta[b]furan-2-ol in 50 ml of HMPA was added via a double-tipped needle. After stirring 1 hr at RT, 2.5 ml of acetic acid was added and the majority of the HMPA was removed by a bulb to bulb distillation at 80°–90°/0.2 mm. The residual brown slug was dissolved in 300 ml of water. Sodium hydroxide (5.3 g) was added and the mixture stirred overnight at RT. The ppt. of triphenylphosphine oxide was filtered and the filtrate acidified to pH 5 with 2 N HCl. Ether extraction gave 5.63 g of material after evaporation to constant wt. Purification by column chromatography on silica gel (0–25% EtOAc/bz) gave 3.06 g (78%) of nat-11R,16,16-trimethyl-15R-(2-tetrahydropyranyloxy)-9S-hydroxy-prosta-cis-5,trans-13-dienoic acid as a colorless oil; $[\alpha]_D + 3.12°$ (1% in $CH_3CN$).

Calc. for $C_{28}H_{48}O_5$: C 72.37, H 10.41; Found: C 72.27, H 10.47.

EXAMPLE 11

Nat-11R,16,16-trimethyl-9S,15R-dihydroxyprosta-cis-5,trans-13-dienoic acid

Nat-11R,16,16-trimethyl-15R-(2-tetrahydropyranyloxy)-9S-hydroxyprosta-cis-5,trans-13-dienoic acid (500 mg) was warmed at 40° C. for 18 hr. with 50 ml of a mixture of acetic acid-water-tetrahydrofuran (55-30-15). After this time, the solvent was evaporated at reduced pressure and the residual oil purified by column chromatography on silica gel using 0–60% ethyl acetate/benzene as the eluent to give 400 mg (97%) of nat-11R,16,16-trimethyl-9S,15R-dihydroxyprosta-cis-5,trans-13-dienoic acid as a colorless oil; $[\alpha]_D + 53.04°$ (0.6% in $CH_3CN$).

Calc. for $C_{23}H_{40}O_4$: C 72.59, H 10.60; Found: C 71.94, H 10.87.

EXAMPLE 12

Nat-11R,16,16-trimethyl-15R-hydroxy-9-oxoprosta-cis-5,trans-13-dienoic acid

To a rapidly stirred solution of 650 mg (1.4 mmol) of nat-11R,16,16-trimethyl-15R-(2-tetrahydropyranyloxy)-9S-hydroxy-prosta-cis-5,trans-13-dienoic acid in 100 ml of ether-acetone (4:1) at RT was added 80 drops of 2.0 M Jones reagent ($CrO_3$-$H_2SO_4$). After 20 min, the reaction was diluted with ether (150 ml) and washed with 20 ml portions of water until neutral. The organic solution was dried ($MgSO_4$) and evaporated to dryness to give 658 mg of crude nat-11R,16,16-trimethyl-15R-(2-tetrahydropyranyloxy)-9-oxoprosta-cis-5,trans-13-dienoic acid as a light yellow oil. This oil was mixed with 50 ml of a mixture of acetic acid-water-THF (55-30-15) and warmed to 40° C. for 20 hr. After this time, the solvent was evaporated and the residual oil purified by column chromatography on silica gel (0–50% EtOAc/bz) to give 523 mg (98%) of nat-11R,16,16-trimethyl-15R-hydroxy-9-oxoprosta-cis-5,trans-13-dienoic acid as a colorless oil: $[\alpha]_D - 51.54°$ (1% in $CHCl_3$).

Calc. for $C_{28}H_{46}O_5$: C 72.69, H 10.02; Found: C 73.02, H 10.15.

EXAMPLE 13

Methyl nat-11R,16,16-trimethyl-15R-hydroxy-9-oxoprosta-cis-5,trans-13-dienoate

To 500 mg (1.3 mmol) of nat-11R,16,16-trimethyl-15R-hydroxy-9-oxoprosta-cis-5,trans-13-dienoic acid in 50 ml of ether was added distilled diazomethaneether until the yellow color persisted longer than 5 min. The solvent was evaporated and the product twice purified by high pressure liquid chromatography using first 25% EtOAc/hexane followed by 20% EtOAc/benzene to give 480 mg (93%) of methyl nat-11R,16,16-trimethyl-15R-hydroxy-9-oxoprosta-cis-5,trans-13-dienoate as a colorless oil; $[\alpha]_D - 51.63°$ (1% in $CH_3CN$).

Calc. for $C_{24}H_{40}O_4$: C 73.43, H 10.27; Found: C 73.35, H 10.33.

EXAMPLE 14

3,3aR,4,5,6,6aS-Hexahydro-4R-[4,4-dimethyl-3S(2-tetrahydropyranyloxy)-1-trans-octenyl]-5R-methyl-2H-cyclopenta[b]furan-2-ol By the procedure of Example 9, 3,3aR,4,5,6,6aS-hexahydro-4R-(4,4-dimethyl-3S-hydroxy-1-trans-octenyl)-5R-methyl-2H-cyclopenta[b]furan-2-one was converted to 3,3aR,4,5,6,6aS-hexahydro-4R-[4,4-dimethyl-3S-(2-tetrahydropyranyloxy)-1-trans-octenyl]-5R-methyl-2H-cyclopenta[b]furan-2-ol; a colorless oil, $[\alpha]_D - 38.34°$ (1% in $CH_3CN$).

Calc. for $C_{23}H_{40}O_4$: C 72.59, H 10.59; Found: C 72.76, H 10.50.

EXAMPLE 15

Nat-11R,16,16-trimethyl-15S-(2-tetrahydropyranyloxy)-9S-hydroxy-prosta-cis-5,trans-13-dienoic acid By the procedure of Example 10, 3,3aR,4,5,-6,6aS-hexahydro-4R-[4,4-dimethyl-3S-(2-tetrahydropyranyloxy)-1-trans-octenyl]-5R-methyl-2H-cyclopenta[b]furan-2-ol was converted to nat-11R,16,16-trimethyl-15S-(2-tetrahydropyranyloxy)-9S-hydroxy-prosta-cis-5,trans-13-dienoic acid; a colorless oil, $[\alpha]_D + 40.39°$ (1% in $CH_3CN$).

Calc. for $C_{28}H_{48}O_5$: C 72.37, H 10.41; Found: C 72.54, H 10.49.

EXAMPLE 16

Nat-11R,16,16-trimethyl-9S,15S-dihydroxyprosta-cis-5,trans-13-dienoic acid

By the procedure of Example 11, nat-11R,16,16-trimethyl-15S-(2-tetrahydropyranyloxy)-9S-hydroxy-prosta-cis-5,trans-13-dienoic acid was converted to nat-11R,16,16-trimethyl-9S,15S-dihydroxyprosta-cis-5,trans-13-dienoic acid; a colorless oil, $[\alpha]_D + 12.4°$ (0.5% in $CH_3CN$).

Calc. for $C_{13}H_{40}O_4$: C 72.59, H 10.60; Found: C 72.32, H 10.83.

EXAMPLE 17

Nat-11R,16,16-trimethyl-15S-hydroxy-9-oxoprosta-cis-5,trans-13-dienoic acid

By the procedure of Example 12, nat-11R,16,16-trimethyl-15S-(2-tetrahydropyranyloxy)-9S-hydroxyprosta-cis-5,trans-13-dienoic acid was converted to nat-11R,16,16-trimethyl-15S-hydroxy-9-oxoprosta-cis-5,trans-13-dienoic acid; a colorless oil, $[\alpha]_D - 83.70°$ (1% in CH$_3$CN).

Calc. for $C_{23}H_{38}O_4$: C 72.97, H 10.12; Found: C 72.88, H 10.12.

EXAMPLE 18

3,3aS,4,5,6,6aR-Hexahydro-4R-nitromethyl-5S-hydroxymethyl-2H-cyclopenta[b]furan-2-one By the procedure of Example 3, the compound 3,3aS,4,5,6,6aR-hexahydro-4R-nitromethyl-5S-carboxy-2H-cyclopenta[b]furan-2-one was converted to 3,3aS,4,5,6,6aR-hexahydro-4R-nitromethyl-5S-hydroxymethyl-2H-cyclopenta[b]furan-2-one as a colorless oil; $[\alpha] + 32.72°$ (1% in dioxane).

Calc. for $C_9H_{13}NO_5$: C 50.23, H 6.09, N 6.51; Found: C 50.26, H 6.12, N 6.70.

EXAMPLE 19

3,3aS,4,5,6,6aR-Hexahydro-4R-nitromethyl-5S-methyl-2H-cyclopenta[b]furan-2-one

By the procedure of Example 4, 3,3aS,4,5,6,6aR-hexahydro-4R-nitromethyl-5-S-hydroxymethyl-2H-cyclopenta[b]furan-2-one was converted to 3,3aS,4,5,6,6aR-hexahydro-4R-nitromethyl-5S-methyl-2H-cyclopenta[b]furan-2-one, a colorless oil, $[\alpha]_D + 49.15°$ (1% in CH$_3$CN).

Calc. for $C_9H_{13}NO_4$: C 54.27, H 6.58, N 7.03; Found: C 54.10, H 6.65, N 6.97.

EXAMPLE 20

3,3aS,4,5,6,6aR-Hexahydro-4R-dimethoxymethyl-5S-methyl-2H-cyclopenta[b]furan-2-one By the procedure of Example 5, 3,3aS,4,5,6,6aR-hexahydro-4R-nitromethyl-5S-methyl-2H-cyclopenta[b]furan-2-one was converted to 3,3aS,4,5,6,6aR-hexahydro-4R-dimethoxymethyl-5S-methyl-2H-cyclopenta[b]furan-2-one; a colorless oil $[\alpha]_D + 35.68°$ (1% in CH$_3$CN).

Calc. for $C_{11}H_{18}O_4$: C 61.66, H 8.47; Found: C 61.44; H 8.49.

EXAMPLE 21

3,3aS,4,5,6,6aR-Hexahydro-4R-formyl-5S-methyl-2H-cyclopenta[b]furan-2-one

By the procedure of Example 6, 3,3aS,4,5,6,6aR-hexahydro-4R-dimethoxymethyl-5S-methyl-2H-cyclopenta[b]furan-2-one was converted to 3,3aS,4,5,6,6aR-hexahydro-4R-formyl-5S-methyl-2H-cyclopenta[b]furan-2-one; a colorless oil.

EXAMPLE 22

3,3aS,4,5,6,6aR-Hexahydro-4S-(4,4-dimethyl-3-oxo-1-trans-octenyl)-5S-methyl-2H-cyclopenta[b]furan-2-one By the procedure of Example 7, 3,3aS,4,5,6,6aR-hexahydro-4R-formyl-5S-methyl-2H-cyclopenta[b]furan-2-one was converted to 3,3aS,4,5,6,6aR-hexahydro-4S-(4,4-dimethyl-3-oxo-1-trans-octenyl)-5S-methyl-2H-cyclopenta[b]furan-2-one; a colorless solid mp 57°-8°, $[\alpha]_D - 15.16°$ (1% in CHCl$_3$).

Calc. for $C_{18}H_{28}O_3$: C 73.94, H 9.65; Found: C 73.87, H 9.49.

EXAMPLE 23

3,3aS,4,5,6,6aR-Hexahydro-4S-(4,4-dimethyl-3S-hydroxy-1-trans-octenyl)-5S-methyl-2H-cyclopenta[b]furan-2-one and
3,3aS,4,5,6,6aR-Hexahydro-4S-(4,4-dimethyl-3R-hydroxy-1-trans-octenyl)-5S-methyl-2H-cyclopenta[b]furan-2-one By the procedure of Example 8, 3,3aS,4,5,6,6aR-hexahydro-4S-(4,4-dimethyl-3-oxo-1-trans-octenyl)-5S-methyl-2H-cyclopenta[b]furan-2-one was converted to 3,3aS,4,5,6,6aR-hexahydro-4S-(4,4-dimethyl-3S-hydroxy-1-trans-octenyl)-5S-methyl-2H-cyclopenta[b]furan-2-one; a colorless oil, $[\alpha]_D - 18.13°$ (1% in CH$_3$CN).

Calc. for $C_{18}H_{30}O_3$: C 73.43, H 10.27; Found: C 73.23, H 10.50.

and 3,3aS,4,5,6,6aR-hexahydro-4S-(4,4-dimethyl-3R-hydroxy-1-trans-octenyl)-5S-methyl-2H-cyclopenta[b]furan-2-one; a colorless oil, $[\alpha]_D + 39.83°$ (1% in CH$_3$CN).

Calc. for $C_{18}H_{30}O_3$: C 73.43, H 10.27; Found: C 73.41, H 10.10.

EXAMPLE 24

3,3aS,4,5,6,6aR-Hexahydro-4S-[4,4-dimethyl-3S-(2-tetrahydropyranyloxy)-1-trans-octenyl]-5S-methyl-2H-cyclopenta[b]furan-2-ol By the procedure of Example 9, 3,3aS,4,5,6,6aR-hexahydro-4S-(4,4-dimethyl-3S-hydroxy-1-trans-octenyl)-5S-methyl-2H-cyclopenta[b]furan-2-one was converted to 3,3aS,4,5,6,6aR-hexahydro-4S-[4,4-dimethyl-3S-(2-tetrahydropyranyloxy)-1-trans-octenyl]-5S-methyl-2H-cyclopenta[b]furan-2-ol; a colorless oil, $[\alpha]_D$ zero (1% in CH$_3$CN).

Calc. for $C_{23}H_{40}O_4$: C 72.59, H 10.59; Found: C 72.60, H 10.42.

EXAMPLE 25

Ent-11S,16,16-Trimethyl-15S-(2-tetrahydropyranyloxy)-9R-hydroxyprosta-cis-5,trans-13-dienoic acid By the procedure of Example 10, 3,3aS,4,5,6,6aR-hexahydro-4S-[4,4-dimethyl-3S-(2-tetrahydropyranyloxy)-1-trans-octenyl]-5S-methyl-2H-cyclopenta[b]furan-2-ol was converted to ent-11S,16,16-trimethyl-15S-(2-tetrahydropyranyloxy)-9R-hydroxyprosta-cis-5,trans-13-dienoic acid; a colorless oil, $[\alpha]_D - 28.67°$ (1% in CH$_3$CN)

Calc. for $C_{28}H_{48}O_5$: C 72.37, H 10.41; Found: C 72.24, H 10.46.

EXAMPLE 26

Ent-11S,16,16-Trimethyl-9R,15S-dihydroxyprosta-cis-5,trans-13-dienoic acid

By the procedure of Example 11, ent-11S,16,16-trimethyl-15S-(2-tetrahydropyranyloxy)-9R-hydroxyprosta-cis-5,trans-13-dienoic acid was converted to ent-11S,16,16-trimethyl-9R,15S-dihydroxyprosta-cis-5,trans-13-dienoic acid; a colorless oil, $[\alpha]_D - 47.74°$ (1% in CH$_3$CN).

Calc. for C₂₃H₄₀O₄: C 72.59, H 10.60; Found: C 71.93, H 10.57.

EXAMPLE 27

Ent-11S,16,16-Trimethyl-15S-hydroxy-9-oxoprosta-cis-5,trans-13-dienoic acid

By the procedure of Example 12, ent-11S,16,16-trimethyl-15S-(2-tetrahydropyranyloxy)-9R-hydroxyprosta-cis-5,trans-13-dienoic acid was converted to ent-11S,16,16-trimethyl-15S-hydroxy-9-oxoprosta-cis-5,trans-13-dienoic acid; a colorless oil, $[\alpha]_D + 63.9°$ (1% in CHCl₃).

Calc. for C₂₃H₃₈O₄: C 72.97, H 10.12; Found: C 73.03, H 10.19.

EXAMPLE 28

3,3aS,4,5,6,6aR-Hexahydro-4S-[4,4-dimethyl-3R-(2-tetrahydropyranyloxy)-1-trans-octenyl]-5S-methyl-2H-cyclopenta[b]furan-2-ol By the procedure of Example 9, 3,3aS,4,5,6,6aR-hexahydro-4S-(4,4-dimethyl-3R-hydroxy-1-trans-octenyl)-5S-methyl-2H-cyclopenta[b]furan-2-one was converted to 3,3aS,4,5,6,6aR-Hexahydro-4S-[4,4-dimethyl-3R-(2-tetrahydropyranyloxy)-1-trans-octenyl]-5S-methyl-2H-cyclopenta[b]furan-2-ol; a colorless oil, $[\alpha]_D - 10.32°$ (1% in CH₃CN).

Calc. for C₂₃H₄₀O₄: C 72.59, H 10.59; Found: C 72.44, H 10.47.

EXAMPLE 29

Ent-11S,16,16-Trimethyl-15R-(2-tetrahydropyranyloxy)-9R-hydroxyprosta-cis-5,trans-13-dienoic acid By the procedure of Example 10, 3,3aS,4,5,6,6aR-hexahydro-4S-[4,4-dimethyl-3R-(2-tetrahydropyranyloxy)-1-trans-octenyl]-5S-methyl-2H-cyclopenta[b]furan-2-ol was converted to ent-11S,16,16-trimethyl-15R-(2-tetrahydropyranyloxy)-9R-hydroxyprosta-cis-5,trans-13-dienoic acid; a colorless oil $[\alpha]_D - 53.52°$ (1% in CH₃CN).

Calc. for C₂₈H₄₈O₅: C 72.37, H 10.41; Found: C 72.22, H 10.60.

EXAMPLE 30

Ent-11S,16,16-Trimethyl-9R,15R-dihydroxyprosta-cis-5,trans-13-dienoic acid

By the procedure of Example 11, ent-11S,16,16-trimethyl-15R-(2-tetrahydropyranyloxy)-9R-hydroxyprosta-cis-5,trans-13-dienoic acid was converted to ent-11S,16,16-trimethyl-9R,15R-dihydroxyprosta-cis-5,trans-13-dienoic acid; a colorless oil, $[\alpha]_D - 7.07°$ (1% in CH₃CN).

Calc. for C₂₃H₄₀O₄: C 72.59, H 10.60; Found: C 72.25, H 10.69.

EXAMPLE 31

Ent-11S,16,16-Trimethyl-15R-hydroxy-9-oxoprosta-cis-5,trans-13-dienoic acid

By the procedure of Example 12, ent-11S,16,16-trimethyl-15R-(2-tetrahydropyranyloxy)-9R-hydroxyprosta-cis-5,trans-13-dienoic acid was converted to ent-11S,16,16-trimethyl-15R-hydroxy-9-oxoprosta-cis-5,trans-13-dienoic acid; a colorless solid, mp 54°-5° C., $[\alpha]_D + 123.96°$ (1% in CHCl₃).

Calc. for C₂₃H₃₈O₄: C 72.97, H 10.12; Found: C 73.02, H 10.00.

EXAMPLE 32

2-Fluorahexanoic acid

To a suspension of sodium hydride (1.08 mol) in 1200 ml of toluene was added dropwise 235 g (1.08 mol) of diethyl n-butylmalonate. To the resulting clear solution of the sodium salt was then bubbled perchloryl fluoride while the the temperature was maintained below 10° C. When the calculated amount of perchloryl fluoride had been added a stream of argon was bubbled through the solution for a short period of time. The mixture was filtered and the toluene removed under reduced pressure. The remaining oil was distilled to give 223 g, b.p. 78° (0.1 mmHg) of diethyl-2-fluoro-n-butylmalonate.

To a solution of 500 ml of 4 N aqueous sodium hydroxide was added 223 g of diethyl-2-fluoro-n-butylmalonate and the mixture stirred for 4 hr. At the end of this time the mixture was placed under vacuum at 40° C. and most of the alcohol removed. The mixture was then acidified to pH 2, salted and extracted with a 1:1 solution of ether-pentane. The organic layer was dried and the residue decarboxylated at 150° for 4 hr. The residue was dissolved in pentane, charcoaled and dried. The pentane was removed under vacuum at 10° C. and the residue distilled to give 2-fluoro hexonoic acid b.p. 75° (16 mmHg).

EXAMPLE 33

N-[(S)-alpha-methyl-p-nitrobenzyl]-alpha-fluoro-R-hexanamide and

N-[(S)-alpha-methyl-p-nitrobenzyl]-alpha-fluoro-S-hexanamide

To 50 g of 2-fluoro hexonoic acid was added 3 eq. of thionyl chloride. After stirring for 1 hr. at room temperature, the mixture was heated to 60°-65° and stirred at this temperature for 3 hr. The residual thionyl chloride was removed under vacuum and the residue distilled to give 2-fluoro hexanoyl-chloride b.p. 50-55 (20 mmHg).

To a solution of 2 eq. of S(−)2-methyl-p-nitro benzylamine in ether at 0° was added dropwise a solution of 2-fluoro hexanoylchloride in ether. After the addition was complete, the amine salt was filtered. The ether layer washed with dilute acid and then dried. The ether was removed under reduced pressure and the residual amides separated via high pressure liquid chromatography to give N-[(S)-alpha-methyl-p-nitrobenzyl]-alpha-fluoro-(S)-hexanamide mp 92°-93.5° $[\alpha]_D^{25} - 124.29°$ (CHCl₃) and N-[(S)-alpha-methyl-p-nitrobenzyl]-alpha-fluoro-(R)-hexanamide mp 84.5°-86.5°, $[\alpha]_D^{25} - 66.25°$ (CHCl₃).

EXAMPLE 34

N-[(S)-alpha-Methyl-p-aminobenzyl]alpha-fluoro-R-hexanamide

A mixture of 19 g of N-[(S)-alpha-methyl-p-nitrobenzyl]alpha-fluoro-R-hexanamide, 0.5 g of 10% Pd/C and 250 ml and ethanol was hydrogenated until the theoretical uptake of hydrogen had been completed. The mixture was filtered and the solvents removed under reduced pressure. Crystallization of the residue from hexane-ether afforded N-[(S)-alpha-methyl-p-aminobenzyl]alphafluoro R-hexanamide mp 86°-88° C. $[\alpha]_D^{25} - 111.78$ (CHCl₃).

EXAMPLE 35

N-[(S)-alpha-Methyl-p-aminobenzyl]alpha-fluoro-S-hexanamide

Starting from N-[(S)alpha-methyl-p-nitrobenzyl]alpha-fluoro-S-hexanamide by the procedure in Example 34 was obtained N-[(S)-alpha-methyl-p-aminobenzyl]alpha-fluoro-S-hexanamide mp 80°–82° $[\alpha]_D^{25} -151.58$ (CHCl$_3$).

EXAMPLE 36

2R-Fluoro hexanoic acid methyl ester

A mixture of 169 g of N-[(S)-alpha-methyl-p-aminobenzyl]alpha-fluoro-R-hexanamide and 170 ml of 30% sulfuric acid was heated at 90° for 10 hr. The mixture was cooled and extracted with pentane. The pentane solution was dried and the solvent removed under reduced pressure of 10°. The residue was then treated with an ethereal solution of diazomethane, stirred for 1 hr. and the solvents removed under vacuum. The residue was then distilled to give 2R-fluoro hexanoic acid methyl ester b.p. 72°–74° (16 mmHg); $[\alpha]_D^{25} +12.7°$ (CHCl$_3$).

EXAMPLE 37

2S-Fluoro hexanoic acid methyl ester

By the procedure described in Example 36 from N[(S)-alpha-methyl-p-aminobenzyl]alpha-fluoro-S-hexanamide was obtained 2S-fluoro-hexanoic acid methyl ester b.p. 70°–72° (20 mmHg) $[\alpha]_D^{25} -12.97°$ (CHCl$_3$).

EXAMPLE 38

Dimethyl-(2-oxo-3S-fluoroheptyl)phosphonate

To a solution of 15.1 g of methyl dimethylphosphonate in 120 ml. dry THF was added with stirring at −78°. 1 eq. of butyl lithium in hexane. After stirring for 0.5 hr at this temperature, 8 g of 2S-fluoro hexanoic acid methyl ester was added and the mixture stirred at −78° C. for 1 hr and then allowed to warm to 0°. Pentane (200 ml) and 27.5 ml of 4 N H$_2$SO$_4$ was added and the mixture separated. The aqueous phase was extracted with pentane and the organic layers combined and dried. The solvent was removed under reduced pressure and the residue distilled to give 11.2 g of dimethyl-(2-oxo-3S-fluoroheptyl)phosphonate b.p. 98° (0.2 mmHg), $[\alpha]_D^{25} -63.03$ (CHCl$_3$).

EXAMPLE 39

Dimethyl-(2-oxo-3R-fluoroheptyl)phosphonate

By the procedure described in Example 38, 2R-fluoro-hexanoic acid methyl ester was converted to dimethyl-(2-oxo-3R-fluoroheptyl)phosphonate b.p. 98° (0.2 mmHg), $[\alpha]_D^{25} +63.61$ (CHCl$_3$).

EXAMPLE 40

2-Fluoro-2-methylhexanoic acid ethyl ester

To a solution of 0.9 mol of lithium cyclohoxyl isopropryl amide in one liter of THF was added 100 g of 2-fluoro hexonoic acid ethyl ester at −78°. After stirring for 20 min. at this temperature was added 116 ml of methyl iodide. After 1 hr. one liter of pentane was added and the mixture acidified to pH3 with 1 N H$_2$SO$_4$. The organic layer was separated and washed with saturated aqueous NaCl solution and dried. The solvent was removed under reduced pressure and the residue distilled to give 2-fluoro-2-methylhexanoic acid ethyl ester b.p. 115° (87 mmHg).

EXAMPLE 41

2R-Fluoro-2-methyl-N-[(S)-beta-hydroxy-(S)-alpha-(methoxymethyl)-phenethyl]hexanamide and 2S-fluoro-2-methyl-N-[(S)-beta-hydroxy-(S)-alpha-(methoxy methyl)-phenethyl]hexanamide To a solution of 71 g of 2-fluoro-2-methyl hexanoic acid ethyl ester in 500 ml of glyme was added 1.1 eq. of 1 N sodium hydroxide solution. After stirring for 3.5 hr., the glyme was removed under vacuum, the residue extracted with ether and the aqueous layer acidified. The mixture was then extracted with pentane and the pentane solution dried. The solvent was then removed under vacuum to give 61 g of crude acid. The crude acid was treated with 156 g of oxalyl chloride and the solution stirred at room temperature for 1.5 hr and then heated at 65° for 1.5 hr. The excess oxalyl chloride was then removed under vacuum and the residue distilled to give 51 g of 2-fluoro-2-methylhexanoyl chloride b.p. 60° (25–30 mmHg).

To a solution of 42.1 g (0.233 mol) of (1S,2S)-1-phenyl-2-amino-3-methoxy-1-propanol and 32 ml (0.23 mol) of triethylamine in 2 liters of ether was added dropwise at 0° with stirring 38.7 g of acid chloride in 400 ml of ether. After stirring for 3 hr. at 0°, the amine salt was filtered and the ether solution washed with dilute acid. The ether solution was dried and the solvents removed under reduced pressure. The residue was then separated via high pressure liquid chromatography to give 36 g of 2S-fluoro-2-methyl-N-[(S)-beta-hydroxy-(S)-alpha-(methoxymethyl)-phenethyl[hexanamide mp 76°–77.5° C. $[\alpha]_D^{25} +17.50°$ and 37 g of 2R-fluoro-2-methyl-N[(S)-beta-hydroxy-(S)-alpha-(methoxymethyl)phenethyl[hexanamide mp 94°–96° C. $[\alpha]_D^{25} +31.10$ (CHCl$_3$).

EXAMPLE 42

2R-Fluoro-2-methyl hexanoic acid methyl ester

A mixture of 35 g of 2R-fluoro-2-methyl-N-[(S)-beta-hydroxy-(S)-alpha(methoxymethyl)-phenethyl]]hexanamide and 525 ml of 4 N HCl was refluxed for 4 hr. At the end of this time, the mixture was cooled ether added and the ether solution separated and dried. The ether was removed under vacuum to give 18.3 g of crude acid. The crude acid was then added to an excess of diazomethane in ether and the solution stirred at 0° for 1 hr. The excess diazomethane was treated with acetic acid and the ether solution washed with 5% sodium bicarbonate solution and dried. The ether was removed under vacuum to give 2R-fluoro-2-methyl hexanoic acid methyl ester b.p. 72°–73° (22 mmHg) $[\alpha]_D^{25} +4.1$ (CHCl$_4$).

EXAMPLE 43

2S-Fluoro-2-methyl hexanoic acid methyl ester

By the procedure described in Example 42, 2S-fluoro-2-methyl-N-[(S)-beta-hydroxy-(S)-alpha-(methoxymethyl)-phenethyl]hexanamide was converted to 2S-fluoro-2-methyl hexanoic acid methyl ester b.p. 71° (22 mmHg) $[\alpha]_D^{25} -4.6$ (CHCl$_3$).

EXAMPLE 44

Dimethyl-(2-oxo-3R-fluoro-3-methylheptyl)phosphonate

To a solution of 23.2 g (0.187 mol) of methyl dimethyl phosphonate in 200 ml of dry THF was added 85 ml of 2.1 N butyl lithium in hexane at −78°. After stirring for 0.5 hr, 13.8 g of 2R-fluoro-2-methyl hexanoic acid methyl ester was added at −78°. After 0.5 hr. at this temperature, the reaction was allowed to warm to 0°. Acid (4 N H$_2$SO$_4$) was then added to pH7. The THF removed under reduced pressure and the residue extracted with ether. The ether solution was dried and the solvent removed under reduced pressure to give 19.6 g of dimethyl-(2-oxo-3R-fluoro-3-methylheptyl)phosphonate b.p. 88°–91° (0.1 mmHg) $[\alpha]_D^{25}$ +49.15 (CHCl$_3$).

EXAMPLE 45

Dimethyl-(2-oxo-3S-fluoro-3-methylheptyl)phosphonate

By the procedure described in Example 44, 2S-2-methylhexanoic acid methyl ester was converted to dimethyl-(2-oxo-3S-fluoro-3-methylheptyl)phosponate b.p. 87 (0.1 mmHg) $[\alpha]_D^{25}$ −49.0 (CHCl$_3$).

EXAMPLE 46

3,3aR,4,5,6,6aS-Hexahydro-4R-(4S-fluoro-3-oxo-1-trans-octenyl)-5R-methyl-2H-cyclopenta[b]furan-2-one By the procedure of example 7,3,3aR,4,5,6,6aS-hexahydro-4S-formyl-5R-methyl-2H-cyclopenta[b]furan-2-one was reacted with dimethyl-(2-oxo-3S-fluoroheptyl)phosphonate to give 3,3aR,4,5,6,6aS-hexahydro-4R-(4S-fluoro-3-oxo-1-trans-octenyl)-5R-methyl-2H-cyclopenta[b]furan-2-one as a colorless viscous oil. Structure in agreement with mass spectrum.

EXAMPLE 47

3,3aR,4,5,6,6aS-Hexahydro-4R-(4S-fluoro-3S-hydroxy-1-trans-octenyl)-5R-methyl-2H-cyclopenta[b]furan-2-one- and
3,3aR,4,5,6,6aS-hexahydro-4R(4S-fluoro-3R-hydroxy-1-trans-octenyl)-5R-methyl-2H-cyclopenta[b]furan-2-one By the procedure of example 8, 3,3aR,4,5,6,6aS-hexahydro-4R-(4S-fluoro-3-oxo-1-trans-octenyl)-5R-methyl-2H-cyclopenta[b]furan-2-one was converted to 3,3aR,4,5,6,6aS-hexahydro-4R-(4S-fluoro-3S-hydroxy-1-transoctenyl)-5R-methyl-2H-cyclopenta[b]furan-2-one a light yellow viscous oil and 3,3aR,4,5,6,6aS-hexahydro-4R-(4S-fluoro-3R-hydroxy-1-trans-octenyl)-5R-methyl-2H-cyclopenta[b]furan-2-one a light yellow viscous oil. The mass spectra data is in agreement with structure indicated.

EXAMPLE 48

3,3-aR,4,5,6,6aS-Hexahydro-4R-[4S-fluoro-3R-(2-tetrahydropyranyloxy)-1-trans-octenyl]-5R-methyl-2H-cyclopenta[b]furan-2-one By the procedure of example 9, 3,3aR,4,5,6,6aS-hexahydro-4R-(4S-fluoro-3R-hydroxy-1-trans-octenyl)-5R-methyl-2H-cyclopenta[b]furan-2-one was converted to 3,3aR,4,5,6,6aS-hexahydro-4R-[4S-fluoro-3R-(2-tetrahydropyranyloxy)-1-trans-octenyl]-5R-methyl-2H-cyclopenta[b]furan-2-one a light yellow viscous oil. The mass spectra is in agreement with the structure indicated.

EXAMPLE 49 nat. 11R-methyl-16S-fluoro-15R-(2-tetrahydropyranyloxy)-9S-hydroxyprosta-cis-5-trans-13-dienoic acid By the procedure of example 9, 3,3aR,4,5,6,6aS-hexahydro-4R-[4S-fluoro-3R-(2-tetrahydropyranyloxy)-1-trans-octenyl]-5R-methyl-2H-cyclopenta[b]furan-2-one was converted to 3,3aR,4,5,6,6aS-hexahydro-4R-[4S-fluoro-3R-(2-tetrahydropyranyloxy)-1-trans-octenyl]-5R-methyl-2H-cyclopenta[b]furan-2-ol, a light yellow viscous oil.

By the procedure of example 10, crude 3,3aR,4,5,6-,6aS-hexahydro-4R-[4S-fluoro-3R-(2-tetrahydropyranyloxy)-1-trans-octenyl]-5R-methyl-2H-cyclopenta[b]furan-2-ol was converted to nat. 11R-methyl-16S-fluoro-15R-(2-tetrahydropyranyloxy)-9S-hydroxyprosta-cis-5-trans-13-dienoic acid, a light yellow viscous oil. The mass spectra data is in agreement with the structure indicated.

EXAMPLE 50 nat. 11R-methyl-16S-fluoro-9S,15R-dihydroxyprosta-cis-5-trans-13-dienoic acid

By the procedure of example 11, nat. 11R-methyl-16S-fluoro-15R-(2-tetrahydropyranyloxy)9S-hydroxyprosta-cis-5-trans-13-dienoic acid was converted to nat. 11R-methyl-16S-fluoro-9S,15R-dihydroxyprosta-cis-5-trans-13-dienoic acid. The mass spectra is in agreement with the structure indicated.

EXAMPLE 51 nat. 11R-Methyl-16S-fluoro-15R-hydroxy-9-oxoprosta-cis-5-trans-13-dienoic acid

By the procedure of example 12, nat. 11R-methyl-16S-fluoro-15R-(2-tetrahydropyranyloxy)9S-hydroxyprosta-cis-5-trans-13-dienoic acid was converted to nat. 11R-methyl-16S-fluoro-15R-hydroxy-9-oxoprosta-cis-5-trans-13-dienoic acid mp 41°–45°, $[\alpha]_D^{25-84.01}$ (CHCl$_3$).

Calc: C 68.45, H 9.03; Found: C 68.46, H 9.25.

EXAMPLE 52

3,3aR,4,5,6,6aS-Hexahydro-4R-(4R-fluoro-3-oxo-1-trans-octenyl)-5R-methyl-2H-cyclopenta[b]furan-2-one By the procedure of example 7, 3,3aR,4,5,6,6aS-hexahydro-4S-formyl-5R-methyl-2H-cyclopenta[b]furan-2-one was reacted with dimethyl-(2-oxo-3R-fluoroheptyl)phosphonate to give 3,3aR,4,5,6,6aS-hexahydro-4R-(4R-fluoro-3-oxo-1-trans-octenyl)-5R-methyl-2H-cyclopenta[b]furan-2-one as a light viscous oil. The mass spectra is in agreement with the structure indicated.

EXAMPLE 53

3,3aR,4,5,6,6aS-Hexahydro-4R-(4R-fluoro-3R-hydroxy-1-trans-octenyl)-5R-methyl-2H-cyclopenta[b]furan-2-one and 3,3aR,4,5,6,6aS-hexahydro-4R-(4R-fluoro-3S-hydroxy-1-trans-octenyl)-5R-methyl-2H-cyclopenta[b]furan-2-one By the procedure of example 8, 3,3aR,4,5,6,6aS-hexahydro-4R(4R-fluoro-3-oxo-1-trans-octenyl)-5R-methyl-2H-cyclopenta[b]furan-2-one was converted to 3,3aR,4,5,6,6aS-hexahydro-4R(4R-fluoro-3S-hydroxy-1-trans-octenyl)-5R-methyl-2H-cyclopenta[b]furan-2-one, mp 84.5°–87°, $[\alpha]_D^{25} - 16.07$ (CHCl$_3$) and 3,3aR,4,5,6,6aS-hexahydro-4R-(4R-fluoro-3R-hydroxy-1-trans-octenyl)-5R-methyl-2H-cyclopenta[b]furan-2-one a light yellow viscous oil. $[\alpha]_D^{25} + 9.71$ (CHCl$_3$).

EXAMPLE 54

3,3aR,4,5,6,6aS-Hexahydro-4R-[4R-fluoro-3R-(2-tetrahydropyranyloxy)-1-trans-octenyl]5R-methyl-2H-cyclopenta[b]furan-2-one By the procedure of example 9, 3,3aR,4,5,6,6aS-hexahydro-4R-(4R-fluoro-3R-hydroxy-1-trans-octenyl-5R-methyl-2H-cyclopenta[b]furan-2-one was converted to 3,3aR,4,5,6,6aS-hexahydro-4R-[4R-fluoro-3R-(2-tetrahydropyranyloxy)-1-trans-octenyl]5R-methyl-2H-cyclopenta[b]furan-2-one a light yellow viscous oil.

EXAMPLE 55

3,3aR,4,5,6,6aS-Hexahydro-4R-[4R-fluoro-3R-(2-tetrahydropyranyloxy)-1-trans-octenyl]-5R-methyl-2H-cyclopenta-[b]furan-2-ol By the procedure of example 9, 3,3aR,4,5,6,6aS-hexahydro-4R-[4R-fluoro-3R-(2-tetrahydropyranyloxy)-1-trans-octenyl]5R-methyl-2H cyclopenta[b]furan-2-one was converted to 3,3aR,4,5,6,6aS-hexahydro-4R-[4R-fluoro-3R-(2-tetrahydropyranyloxy)-1-trans-octenyl]-5R-methyl-2H-cyclopenta[b]furan-2-ol a colorless viscous oil. The mass spectra is in agreement with the structre indicated.

EXAMPLE 56 nat. 11R-Methyl-16R-fluoro-15R-hydroxy-9S-hydroxyprosta-cis-5-trans-13-dienoic acid By the procedure of example 10, 3,3aR,4,5,6,6aS-hexahydro-4R-[4R-fluoro-3R-(2-tetrahydropyranyloxy)-1-trans-octenyl]-5R-methyl-2H-cyclopenta[b]furan-2-ol was converted to nat. 11R-methyl-16R-fluoro-15R-(2-tetrahydropyranyloxy)9S-hydroxyprosta-cis-5-trans-13-dienoic acid. Ths crude product was then converted by the procedure of Example 11, to give nat. 11R-methyl-16R-fluoro-15R-hydroxy-9S-hydroxyprosta-cis-5-trans-13-dienoic acid mp 50°–54°, $[\alpha]_D^{25} + 47.4$ (CHCl$_3$).

Anal. Calcd. for C$_{21}$H$_{35}$FO$_4$— Calc. : C 68.01, H 9.52, F 5.13; Found: C 67.65, H 9.50, F 4.71.

EXAMPLE 57 nat. 11R-Methyl-16R-fluoro-15R-hydroxy-9-oxoprosta-cis-5-trans-13-dienoic acid

By the procedure of example 12, crude nat. 11R-methyl-16R-fluoro-15R-(2-tetrahydropyranyloxy)-9S-hydroxyprosta-cis-5-trans-13-dienoic acid was converted to nat. 11R-methyl-16R-fluoro-15R-hydroxy-9-oxoprosta-cis-5-trans-13-dienoic acid a colorless viscous oil, $[\alpha]_D^{25} - 68.78$ (CHCl$_3$).

Anal. Calcd. for C$_{21}$H$_{33}$FO$_4$— Calc. C 68.45, H 9.03, F 5.16; Found: C 68.03, H 8.93, F 4.92.

EXAMPLE 58

3,3aR,4,5,6,6aS-Hexahydro-4R-(4R-fluoro-4-methyl-3-oxo-1-trans-octenyl)-5R-methyl-2H-cyclopenta[b]furan-2-one By the procedure of example 7, 3,3aR,4,5,6,6aS-hexahydro-4S-formyl-5R-methyl-2H-cyclopenta[b]furan-2-one was reacted with dimethyl-(2-oxo-3R-fluoro-3-methyl heptyl)phosphonate to give 3,3aR,4,5,6,6aS-hexahydro-4R-(4R-fluoro-4-methyl-3-oxo-1-trans-octenyl)-5R-methyl-2H-cyclopenta[b]furan-2-one mp 68°–70°, $[\alpha]_D^{25} + 45.74$ (CHCl$_3$).

EXAMPLE 59

3,3aR,4,5,6,6aS-Hexahydro-4R-(3R-hydroxy-4R-fluoro-4-methyl-1-trans-octenyl)-5R-methyl-2H-cyclopenta[b]furan-2-one and 3,3aR-4,5,6,6aS-Hexahydro-4R-(3S-hydroxy-4R-fluoro-4-methyl-1-trans-octenyl)-5R-methyl-2H-cyclopenta[b]furan-2-one To a solution of 2 g of sodium borohydride in 100 ml of methanol at −30° was added a solution of 9.2 g of 3,3aR,4,5,6,6aS-hexahydro-4R-(4R-fluoro-4-methyl-3-oxo-1-trans-octenyl)-5R-methyl-2H-cyclopenta[b]furan in 50 ml of methanol. After 0.5 hr. at −30°, 1 N sulfuric acid was slowly added to pH6 and the methanol removed under reduced pressure. The residue was extracted with ether and the ether solution dried. The solvent was removed under reduced pressure and the residue chromatographed to give 3,3aR,4,5,6,6aS-hexahydro-4R-(3R-hydroxy-4R-fluoro-4-methyl-1-trans-octenyl)-5R-methyl-2H-cyclopenta[b]furan-2-one mp 55–57.5, $[\alpha]_D^{25} + 7.33$ (CHCl$_3$) and 3,3aR,4,5,6,6aS-hexahydro-4R-(3S-hydroxy-4R-fluoro-4-methyl-1-trans-octenyl)-5R-methyl-2H-cyclopenta[b]furan-2-one, mp 83°–85°, $[\alpha]_D^{25} - 27.18$ (CHCl$_3$).

EXAMPLE 60

3,3aR,4,5,6,6aS-Hexahydro-4R[4R-fluoro-3R-(2-tetrahydropyranyloxy)-1-trans-octenyl]5H-cyclopenta[b]furan-2-one By the procedure of example 9, 3,3aR,4,5,6,6aS-hexahydro-4R-(3R-hydroxy-4R-fluoro-4-methyl-1-trans-octenyl)-5R-methyl-2H-cyclopenta[b]furan-2-one was converted to 3,3aR,4,5,6,6aS-hexahydro-4R-[4R-fluoro-3R-(2-tetrahydropyranyloxy)-1-trans-octenyl]-5R-methyl-2H-cyclopenta[b]furan-2-one.

EXAMPLE 61 nat. 11R-Methyl-16R-fluoro-16-methyl-15R-(2-tetrahydropyranyloxy)-9S-hydroxyprosta-cis-5-trans-13-dienoic acid By the procedure of example 9, 3,3aR,4,5,6,6aS-hexahydro-4R-[4R-fluoro-3R-(2-tetrahydropyranyloxy)-1-trans-octenyl]5R-methyl-2H-cyclopenta[b]furan-2-one was converted to 3,3aR,4,5,6,6aS-hexahydro-4R-[4R-fluoro-3R-(2-tetrahydropyranyloxy)-1-trans-octenyl]5R-methyl-2H-cyclopenta[b]furan-2-ol.

By the procedure of example 10, crude 3,3aR,4,5,6,6aS-hexahydro-4R-[4R-fluoro-3R-(2-tetrahydropyranyloxy)-1-trans-octenyl]5R-methyl-2H-cyclopenta[b]furan-2-ol was converted to nat. 11R-methyl-16R-fluoro-16-methyl-15S-(2-tetrahydropyranyloxy)-9S-hydroxyprosta-cis-5-trans-13-dienoic acid, a white waxy solid.

EXAMPLE 62 nat. 11R,16-Dimethyl-16R-fluoro-9S,15R-dihydroxyprosta-cis-5-trans-13-dienoic acid By the procedure of example 11, nat. 11R-methyl-16R-fluoro-16-methyl-15R-(2-tetrahydropyranyloxy)-9S-hydroxyprosta-cis-5-trans-13-dienoic acid was converted to nat. 11R,16-dimethyl-16R-fluoro-9S,15R-dihydroxyprosta-cis-5-trans-13-dienoic acid, mp 70°–73°, $[\alpha]_D^{25}$ + 42.94° (CHCl$_3$).

Anal. calcd. for $C_{22}H_{37}FO_4$— Calcd.: C 68.72, H 9.70, F 4.94; Found: C 68.78, H 9.70, F 5.08.

EXAMPLE 63 nat. 11R,16-Dimethyl-16R-fluoro-15R-hydroxy-9-oxoprosta-cis-5-trans-13-dienoic acid By the procedure of example 12, nat. 11R-methyl-16R-fluoro-16-methyl-15R-(2-tetrahydropyranyloxy)-9S-hydroxyprosta-cis-5-trans-13-dienoic acid was converted to nat. 11R,16-dimethyl-16R-fluoro-15R-hydroxy-9-oxoprosta-cis-5-trans-13-dienoic acid, a colorless viscous liquid, $[\alpha]_D^{25}$ − 57.55° (CHCl$_3$).

Anal. calcd. for $C_{22}H_{35}FO_4$— Calcd.: C 69.08, H 9.22, F 4.97; Found: C 68.76, H 9.19, F 4.70.

EXAMPLE 64

Ethyl 2-Trifluoromethylhexanoate

To a 4 liter stainless steel bomb was added 237 g. (1.26 mol) of 2-carboethoxyhexanoic acid, 260 ml. of methylene chloride, and 19 ml. of 48% hydrofluoric acid. The bomb was sealed with an assembly consisting of a rupture disk (1400–1600 psi) and a needle valve. It was then cooled in a dry ice-acetone bath for 30 minutes and evacuated to less than 10 mmHg pressure. While maintaining the bomb in the cooling bath, 600 g. (5.56 mol) of sulfur tetrafluoride was condensed into the bomb from an attached lecture bottle. The needle valve closed and the bomb was removed from the cooling bath and allowed to remain at room temperature, with only occasional agitation for 13 days. After this period of time, the bomb was vented and the residual materials taken up in pentane (2.2 liters), dried over NaF/MgSO$_4$. Distillation of the filtered pentane solution gave 117 g. (44%) of ethyl 2-trifluoromethylhexanoate, b.p. 69°–76°/20 mmHg.

EXAMPLE 65

2-Trifluoromethylhexanoic acid

Ethyl 2-trifluoromethylhexanoate (10.05 g.) was mixed with 50 ml. of concentrated sulfuric acid and warmed to 75° C. for 20 hours. After cooling, the acid was poured onto excess ice. The resulting mixture was saturated with sodium chloride, extracted with ether (3 × 100 ml.). The combined ether extracts were dried (MgSO$_4$) and evaporated to give a residual oil which yielded 2-trifluoromethylhexanoic acid (7.50 g.) upon distillation, b.p. 80°–85°/2.8 mmHg.

EXAMPLE 66

2-Trifluoromethylhexanoyl chloride

2-Trifluoromethylhexanoic acid (2.3 g.) was added dropwise to 10 g. oxalyl chloride (10 g.) and the mixture heated to reflux for 2 hours. Distillation of the reaction mixture after this time yielded 2-trifluoromethylhexanoyl chloride (2.27 g.; 90%), b.p. 67°–70°/43 mmHg.

EXAMPLE 67

3-Trifluoromethyl-1-bromoheptan-2-one

2-Trifluoromethylhexanoyl chloride (2.27 g.) was added dropwise to an excess of ethereal diazomethane solution at 0° C. After one hour, the excess diazomethane was removed with a stream of nitrogen. The ether solution at 0° C. was then treated with an excess of hydrogen bromide gas. After 15 minutes, the solution was washed with saturated sodium chloride solution (3 × 10 ml.), dried (MgSO$_4$) and evaporated to constant weight in a vacuum to give 2.56 g. (88%) of 3-trifluoromethyl-1-bromoheptan-2-one, which was not further purified.

EXAMPLE 68

Diethyl (3-trifluoromethyl-2-oxoheptyl)phosphonate

A mixture of 3-trifluoromethyl-1-bromoheptan-2-one (2.50 g.) and triethylphosphite (5.1 g.) was heated to 100° C. and continuously flushed with a slow stream of nitrogen. After 6 hours, the mixture was distilled to give 2.60 g. of a mixture of diethyl (3-trifluoromethyl-2-oxoheptyl)phosphonate and diethyl (3-trifluoromethyl-hepten-1-yl-2)-phosphate. The diethyl (3-trifluoromethyl-2-oxoheptyl)phosphonate was isolated from this mixture.

EXAMPLE 69

Ethyl 2-Trifluoromethyl-2-methylhexanoate

To a 90 ml. stainless steel bomb was added 6.6 g. of 2-carboethoxy-2-methylhexanoic acid, 5 ml. of dichloromethane, and 0.4 ml. of 48% hydrofluoric acid. The bomb was sealed with an assembly consisting of a rupture disk (2400–3600 psig) and a needle valve. The bomb was then cooled in a dry ice-acetone bath and evacuated to less than 10 mmHg pressure. Sulfur tetrafluoride (15 g.) was condensed into the bomb from an attached lecture bottle. The needle valve was closed and the bomb was stored in a hood at room temperature for 3 days. After this time, the bomb was immersed to ½ of its length in a 60° C. bath. After warming at 60° C. for 3 days, the bomb was cooled and vented. The residual materials were taken up in pentane (250 ml.). The pentane solution was dried (NaF/MgSO$_4$), filtered and distilled to give 3.14 g. (42%) of ethyl 2-trifluoromethylhexanoate, b.p. 79°–81°/20 mmHg.

EXAMPLE 70

Diethyl (3-trifluoromethyl-3-methyl-2-oxoheptyl)phosphonate

A 100 ml. flask was charged with 3.34 g. (22 mmol) of methyl diethylphosphonate and 50 ml. of tetrahydrofuran. The flask was sealed with a rubber septum, cooled to −75° C. (dry ice-acetone) and flushed with argon. To the cooled solution was added with stirring 13.7 ml. (22 mmol) of 1.6 M n-butyllithium/hexane. After 10 minutes, 2.26 g. (10 mmol) of ethyl-2-trifluoromethyl-2-methylhexanoate was added and the mixture was allowed to warm to room temperature as the dry ice-acetone bath dissipated (50 minutes). After 2 hours, the reaction was mixed with ether (200 ml.) and 2 N sulfuric acid (20 ml.). The layers were separated and the ether layer was washed with 2×20 ml. of saturated NaCl solution, dried (NaCl/MgSO$_4$), filtered and the filtrate distilled to give 2.79 g. (84%) of diethyl 3-trifluoromethyl-3-methyl-2-methyl-2-oxo-heptylphosphonate, b.p. 94°–97°/0.15 mmHg.

EXAMPLE 71

(2R)-Trifluoromethyl-N-[(1S,2S)-1-phenyl-1-hydroxy-3-methoxy-2-propyl]-hexanamide and (2S)-Trifluoromethyl-N-[(1S,2S)-1-phenyl-1-hydroxy-3-methoxy-2-propyl]hexanamide 2-Trifluoromethylhexanoyl chloride (8.11 g.) was added dropwise to an ice cold solution of triethylamine (4.5 g.) and (1S,2S)-1-phenyl-2-amino-3-methoxypropan-1-ol (6.7 g.) in 350 ml. of ethyl ether. The mixture was stirred for 1 hour at room temperature, filtered and the filtrate washed with 3×10 ml. of 2 N hydrochloric acid. The ether layer was dried (MgSO$_4$) and the ether evaporated in vacuo to give 9.12 g. of a 1:1 mixture (m.p. 65°–76° C.) of (2R)-trifluoromethyl-N-[(1S,2S)-1-phenyl-1-hydroxy-3-methoxy-2-propyl]hexanamide and (2S)-trifluoromethyl-N-[(1S,2S)-1-phenyl-1-hydroxy-3-methoxy-2-propyl]hexanamide, which was separated by silica gel chromatography using 20:1 benzene-ethyl acetate.

EXAMPLE 72

(2R)-2-Trifluoromethyl-2-methyl-N-[(1S,2S)-1-phenyl-1-hydroxy-3-methoxy-2-propyl]hexanamide and (2S)-2-trifluoromethyl-2-methyl-N-[(1S,2S)-1-phenyl-1-hydroxy-3-methoxy-2-propyl]hexanamide By the procedure of Example 41, 2-trifluoromethyl-2-methyl-hexanoyl chloride (2.1 g.) was reacted with (1S,2S)-1-phenyl-2-amino-3-methoxypropan-1-ol (1.5 g.) to give an oily 1:1 mixture of (2R)-2-trifluoromethyl-2-methyl-N-[(1S,2S)-1-phenyl-1-hydroxy-3-methoxy-2-propyl]hexanamide and (2S)-2-trifluoromethyl-2-methyl-N-[(1S,2S)-1-phenyl-1-hydroxy-3-methoxy-2-propyl]hexanamide, which was separated by silica gel chromatography using 20:1 benzene-ethyl acetate.

EXAMPLE 73

(2R)-Trifluoromethylhexanoic acid (2R)-2-Trifluoromethyl-N-[(1S,2S)-1-phenyl-1-hydroxy-3-methoxy-2-propyl]hexanamide (3.5 g.) was heated to 100°–110° C. with 70 ml. of 4.5 N hydrochloric acid. After heating for 2.5 hours, the mixture was cooled, saturated with sodium chloride, and extracted with 3×50 ml. of ethyl ether. The combined ether extracts were dried (MgSO$_4$) and the ether evaporated in a vacuum at 35° C. Distillation of the residual oil gave 1.91 g. of (2R)-trifluoromethylhexanoic acid, b.p. 83°–85°/2.6 mmHg.

EXAMPLE 74

(2S)-Trifluoromethylhexanoic acid

By the procedure of Example 73, (2S)-2-trifluoromethyl-N-[(1S,2S)-1-phenyl-1-hydroxy-3-methoxy-2-propyl]hexanamide was converted to (2S)-trifluoromethylhexanoic acid.

EXAMPLE 75

(2R)-2-Trifluoromethyl-2-methylhexanoic acid

By the procedure of Example 73, (2R)-2-trifluoromethyl-2-methyl-N-[(1S,2S)-1-phenyl-1-hydroxy-3-methoxy-2-propyl]hexanamide was converted to (2R)-2-trifluoromethyl-2-methylhexanoic acid.

EXAMPLE 76

(2S)-2-Trifluoromethyl-2-methylhexanoic acid

By the procedure of Example 73, (2S)-2-trifluoromethyl-2-methyl-N-[(1S,2S)-1-phenyl-1-hydroxy-3-methoxy-2-propyl]hexanamide was converted to (2S)-2-trifluoromethyl-2-methylhexanoic acid.

EXAMPLE 77

3,3abeta,4,5,6,6abeta-hexahydro-4beta-(3-oxo-4-trifluoromethyl-1-trans-octenyl)-5alpha-methyl-2-oxo-2H-cyclopenta[b]furan To a suspension of 0.7 g. of sodium hydride in 150 ml. of diglyme was added 6 g. of dimethyl (3-trifluoromethyl)-2-oxoheptyl)phosphonate. After stirring for 1.5 hours, 5 g. of 3,3abeta,4,5,6,6abeta-hexahydro-4beta-formyl-5alpha-methyl-2-oxo-2H-cyclopenta[b]furan dissolved in 30 ml. of glyme was added dropwise at 0° C. After stirring for 3 hours at room temperature, 500 ml. of diethyl ether was added and the mixture was washed with water. The organic layer was then dried (MgSO$_4$) and the solvent removed under reduced pressure. The residue was then washed through 75 g. of silica gel to give the above-named product.

EXAMPLE 78

3,3abeta,4,5,6,6abeta-Hexahydro-4beta-(3-oxo-4-methyl-4-trifluoromethyl-1-trans-octenyl)-5-alpha-methyl-2-oxo-2H-cyclopenta[b]furan By the procedure of Example 77, 3,3abeta-4,5,6,6abeta-hexahydro-4beta-formyl-5alpha-methyl-2-oxo-2H-cyclopenta[b]furan was reacted with dimethyl (2-oxo-3-methyl-3-trifluoromethylheptyl)phosphonate to give the above-named product.

EXAMPLE 79

3,3abeta,4,5,6,6abeta-Hexahydro-4beta-(3-alpha-hydroxy-4-trifluoromethyl-1-trans-octenyl)-5alpha-methyl-2-oxo-2H-cyclopenta[b]furan and 3,3abeta,4,5,6,6abeta-Hexahydro-4beta-(3beta-hydroxy-4-trifluoromethyl-1-trans-octenyl)-5alpha-methyl-2-oxo-2H-cyclopenta[b]furan To a solution of 4.5 g. of 3,3abeta,4,5,6,6abeta-hexahydro-4beta-(3-oxo-4-trifluoromethyl-1-trans-octenyl)-5alpha-methyl-2-oxo-2H-cyclopenta[b]furan in 100 ml. of diglyme was added an excess of zinc borohydride in 50 ml. of glyme and the resulting solution stirred for 3 hours. The solution was cooled to 0° C. and treated with 200 ml. of water, 400 ml. of ether and 10 ml. of 0.5 N aqueous sulfuric acid. The ether was separated and dried (MgSO$_4$) and the solvent removed under reduced pressure to give 3,3abeta,4,5,6,6abeta-hexahydro-4beta-(3-hydroxy-4-trifluoromethyl-1-trans-octenyl)-5alpha-methyl-2-oxo-2H-cyclopenta[b]furan. Column chromatography on silica gel utilizing diethyl ether hexane (70:30 parts by volume) then afforded first the 3,3abeta,4,5,6,6abeta-hexahydro-4beta-(3-alpha-hydroxy-4-trifluoromethyl-1-trans-octenyl)-5alpha-methyl-2-oxo-2H-cyclopenta[b]furan and then 3,3abeta,4,5,6,6abeta-hexahydro-4beta-(3beta-hydroxy-4-tri-fluoromethyl-1-trans-octenyl)-5alpha-methyl-2-oxo-2H-cyclopenta[b]furan.

EXAMPLE 80

3,3abeta,4,5,6,6abeta-Hexahydro-4beta-(3alpha-hydroxy-4-trifluoromethyl-4-methyl-1-trans-octenyl)-5alpha-methyl-2-oxo-2H-cyclopenta[b]furan and 3,3abeta,4,5,6,6abeta-Hexahydro-4beta-(3beta-hydroxy-4-trifluoromethyl-4-methyl-1-trans-octenyl)-3alpha-methyl-2-oxo-2H-cyclopenta[b]furan By the procedure of Example 79, 3,3abeta,4,5,6,6abeta-hexahydro-4alpha-(3-oxo-4-trifluoromethyl-4-methyl-1-trans-octenyl)-5alpha-methyl-2-oxo-2H-cyclopenta[b]furan was converted to 3,3abeta,4,5,6,6abeta-hexahydro-4beta-(3alpha-hydroxy-4-trifluoromethyl-4-methyl-1-trans-octenyl)-5alpha-methyl-2-oxo-2H-cyclopenta[b]furan and 3,3abeta,4,5,6,6abeta-hexahydro-4beta-(3beta-hydroxy-4-trifluoromethyl-4-methyl-1-trans-octenyl)-3alpha-methyl-2-oxo-2H-cyclopenta[b]furan which were separated by column chromatography in the manner of Example 61.

EXAMPLE 81

3,3abeta,4,5,6,6abeta-Hexahydro-4beta[3alpha-(2-tetrahydropyranyloxy)-4-trifluoromethyl-1-trans-octenyl]-5alpha-methyl-2-oxo-2H-cyclopenta[b]furan A solution of 5 g. of 3,3abeta,4,5,6,6abeta-hexahydro-4beta-(3alpha-hydroxy-4-trifluoromethyl-1-trans-octenyl)-5alpha-methyl-2-oxo-2H-cyclopenta[b]furan, 12 g. of dihydropyran and 25 mg. of p-toluenesulfonic acid in 200 ml. of methylene chloride was stirred at 25° C. for 3 hours. The solution was washed with saturated sodium bicarbonate solution, the methylene chloride solution dried (MgSO4) and the volatile components evaporated under reduced pressure to give 6.4 g. of the above-named product.

EXAMPLE 82

3,3abeta,4,5,6,6abeta-Hexahydro-4beta[3alpha-(2-tetrahydropyranyloxy)-4-trifluoromethyl-4-methyl-1-trans-octenyl]-5alpha-methyl-2-oxo-2H-cyclopenta[b-]furan By the procedure of Example 81, 3,3abeta,4,5,6,6abeta-hexahydro-4beta-(3alpha-hydroxy-4-trifluoromethyl-4-methyl-1-trans-octenyl)-5alpha-methyl-2-oxo-2H-cyclopenta[b]furan was converted to the above-named product.

EXAMPLE 83

3,3abeta,4,5,6,6abeta-Hexahydro-4beta[3alpha-(2-tetrahydropyranyloxy)-4-trifluoromethyl-1-trans-octenyl]-5alpha-methyl-2H-cyclopenta[b]furan-2-ol To a solution of 5.3 g. of 3,3abeta,4,5,6,6abeta-hexahydro-4beta[3alpha-(2-tetrahydropyranyloxy)-4-trifluoromethyl-1-trans-octenyl]-5alpha-methyl-2-oxo-2H-cyclopenta[b]furan in 150 ml. of toluene was added dropwise at −78° C. 1 equivalent of diisobutylaluminum hydride in the same solvent. The reaction mixture was stirred at this temperature for 2 hours after which time 20 ml. of methanol was slowly added and the mixture stirred for 2 hours at room temperature. The mixture was then filtered through a bed of celite, the celite was washed with ethyl acetate and the solvents were then removed under reduced pressure. The residue was then washed through a column of silica gel to give the above-named product.

EXAMPLE 84

3,3abeta,4,5,6,6abeta-Hexahydro-4beta[3alpha-(2-tetrahydropyranyloxy)-4-trifluoromethyl-4-methyl-1-trans-octenyl]-5alpha-methyl-2H-cyclopenta[b]furan-2-ol By the procedure of Example 83, 3,3abeta,4,5,6,6abeta-hexahydro-4beta[3alpha-(2-tetrahydropyranyloxy)-4-trifluoromethyl-4-methyl-1-trans-octenyl]-5alpha-methyl-2-oxo-2H-cyclopenta[b]furan was converted to the above-named product.

EXAMPLE 85

7-(3alpha-methyl-5alpha-hydroxy-2beta[3alpha-(2-tetrahydropyranoyloxy)-4-trifluoromethyl-1-trans-octenyl]-1alpha-cyclopentyl)-cis-5-heptenoic acid 3.6 g. of 3,3abeta,4,5,6,6abeta-hexahydro-4beta-[3alpha-(2-tetrahydropyranyloxy)-4-trifluoromethyl-1-trans-octenyl]-5alpha-methyl-2H-cyclopenta[b]furan-2-ol in 150 ml. of hexamethylphosphoric triamide was reacted with 2.2 equivalents of Wittig reagent generated by the reaction of 7.0 g. (0.0384 mol) of sodium bis-trimethylsilyl amide with 8.4 g. (0.19 mol) of (4-carboxybutyl)-triphenylphosphonium bromide. After stirring for thirty minutes, the mixture was acidified to pH 6.5 with dilute sulfuric acid and the hexamethylphosphoramide removed under high vacuum. The mixture was then extracted several times with ether and the ether solution dried (Na2SO4). The solvent was then removed under reduced pressure and the residue chromatographed on silica gel to give 3.5 g. of the above-named product.

EXAMPLE 86

7-{3alpha-methyl-5alpha-hydroxy-2beta[3alpha-(2-tetrahydropyranyloxy)-4-trifluoromethyl-4-methyl-1-trans-octenyl]-1alpha-cyclopentyl}-cis-5-heptenoic acid By the procedure of Example 85, 3,3abeta,4,5,6,6abeta-hexahydro-4beta-[3alpha-(2-tetrahydropyranyloxy)-4-trifluoromethyl-4-methyl-1-trans-octenyl]-5alpha-methyl-2H-cyclopenta[b]furan-2-ol is converted to the above-named product.

EXAMPLE 87

7-[3alpha-methyl-5-oxo-2beta-(3alpha-hydroxy-4-trifluoromethyl-1-trans-octenyl)-1alpha-cyclopentyl]-cis-5-heptenoic acid To a mixture of 6 g. of chromiun trioxide and 9.5 g. of pyridine in 150 ml. of methylene chloride was added at 0° C. 4.5 g. of 7{3alpha-methyl-5alpha-hydroxy-2beta-[3alpha-(2-tetrahydropyranyloxy)-4-trifluoromethyl-1-trans-octenyl]-1alpha-cyclopentyl}-cis-5-heptenoic acid dissolved in 50 ml. of methylene chloride. The mixture was stirred for 1 hour at room temperature and the mixture filtered through a bed of celite. The celite was washed with methylene chloride and the combined methylene chloride solution washed with dilute hydrochloric acid to remove any remaining pyridine. The methylene chloride was then removed under reduced pressure and the residue treated with 50 ml. of 3:1 parts by volume acetic acid/water solution at 35° C. for 15 hours. The solvents were then removed under high vacuum and the residue purified by column chromatography to give the above-named product.

EXAMPLE 88

7-[3alpha-methyl-5-oxo-2beta-(3alpha-hydroxy-4-trifluoromethyl-4-methyl-1-trans-octenyl)-1alpha-cyclopentyl]-cis-5-heptenoic acid By the procedure of Example 87, 7-{3alpha-methyl-5alpha-hydroxy-2beta-[3alpha-(2-tetrahydropyranyloxy)-4-trifluoromethyl-4-methyl-1-trans-octenyl]-1alpha-cyclopentyl}-cis-5-heptenoic acid was converted to the above-named product.

EXAMPLE 89

7-[3alpha-methyl-5alpha-hydroxy-2beta-(3alpha-hydroxy-4-trifluoromethyl-1-trans-octenyl)-1alpha-cyclopentyl]-cis-5-heptenoic acid A solution of 200 mg. of 7-{3alpha-methyl-5alpha-hydroxy-2beta-[3alpha-(2-tetrahydropyranyloxy)-4-trifluoromethyl-1-trans-octenyl]-1alpha-cyclopentyl}-cis-5-heptenoic acid in 5 ml. of 3:1 parts by volume acetic acid/water solution was kept at 35° C. for 15 hours. The solvent was then removed under high vacuum and the residue purified via column chromatography to give the above-named product.

EXAMPLE 90

7-[3alpha-methyl-5alpha-hydroxy-2beta-(3alpha-hydroxy-4-trifluoromethyl-4-methyl-1-trans-octenyl)-1alpha-cyclopentyl]-cis-5-heptenoic acid By the procedure of Example 89, 7-{3alpha-methyl-5alpha-hydroxy-2beta-[3alpha-(2-tetrahydropyranyloxy)-4-trifluoromethyl-4-methyl-1-trans-octenyl]-1alpha-cyclopentyl}-cis-5-heptenoic acid was converted to the above-named product.

EXAMPLE 91

3,3abeta,4,5,6,6abeta-hexahydro-4beta(3-oxo-4-trifluoromethyl-1-trans-octenyl)-2-oxo-2H-cyclopenta[b]furan By the procedure of Example 77, dimethyl (2-oxo-3-trifluoromethylheptyl) phosphonate was reacted with 3,3abeta,4,5,6,6abeta-hexahydro-4beta-formyl-2-oxo-2H-cyclopenta[b]furan to produce the above-named product.

EXAMPLE 92

3,3abeta,4,5,6,6abeta-hexahydro-4beta-(3-oxo-4-methyl-4-trifluoromethyl-1-trans-octenyl)-2-oxo-2H-cyclopenta[b]furan By the procedure of Example 77, 3,3abeta,4,5,6,6abeta-hexahydro-4beta-formyl-2-oxo-2H-cyclopenta[b]furan was reacted with dimethyl (2-oxo-3-methyl-3-trifluoromethylheptyl)phosphonate to give the above-named product.

EXAMPLE 93

3,3abeta,4,5,6,6abeta-hexahydro-4beta-(3alpha-hydroxy-4-trifluoromethyl-1-trans-octenyl)-2-oxo-2H-cyclopenta[b]furan and
3,3abeta,4,5,6,6abeta-hexahydro-4beta(3beta-hydroxy-4-trifluoromethyl-1-trans-octenyl)-2-oxo-2H-cyclopenta[b]furan By the procedure of Example 79, 3,3abeta,4,5,6,6abeta-hexahydro-4beta-(3-oxo-4-trifluoromethyl-1-trans-octenyl)-2-oxo-2H-cyclopenta[b]furan was reacted to give 3,3abeta,4,5,6,6abeta-hexahydro-4beta-(3-hydroxy-4-trifluoromethyl-1-trans-octenyl)-2-oxo-2H-cyclopenta[b]furan. Chromatography on silica gel in the manner of Example 79 afforded first the 3,3abeta,4,5,6,6abeta-hexahydro-4beta-(3alpha-hydroxy-4-trifluoromethyl-1-trans-octenyl)-2-oxo-2H-cyclopenta[b]furan. Also obtained by chromatography was the 3,3abeta,4,5,6,6abeta-hexahydro-4beta(3beta-hydroxy-4-trifluoromethyl-1-trans-octenyl)-2-oxo-2H-cyclopenta[b]furan.

EXAMPLE 94

By the procedure of Example 79, 3,3abeta,4,5,6,6abeta-hexahydro-4beta-(3-oxo-4-trifluoromethyl-4-methyl-1-trans-octenyl)-2-oxo-2H-cyclopenta[b]furan was converted to 3,3abeta,4,5,6,6abeta-hexahydro-4beta-(3alpha-hydroxy-4-trifluoromethyl-4-methyl-1-trans-octenyl)-2-oxo-2H-cyclopenta[b]furan and 3,3abeta,4,5,6,6abeta-hexahydro-4beta(3beta-hydroxy-4-trifluoromethyl-4-methyl-1-trans-octenyl)-2-oxo-2H-cyclopenta[b]furan which were separated by column chromatography in the same manner as Example 79.

EXAMPLE 95

By the procedure of Example 81, 3,3abeta,4,5,6,6abeta-hexahydro-4beta-[3alpha-hydroxy-4-trifluoromethyl-1-trans-octenyl]-2-oxo-2H-cyclopenta[b]furan was converted to 3,3abeta,4,5,6,6abeta-hexahydro-4beta-[3alpha-(2-tetrahydropyranyloxy)-4-trifluoromethyl-1-trans-octenyl]-2-oxo-2H-cyclopenta[b]furan.

EXAMPLE 96

By the procedure of Example 81, 3,3abeta,4,5,6,6abeta-hexahydro-4beta-(3alpha-hydroxy-4-trifluoromethyl-4-methyl-1-trans-octenyl)-2-oxo-2H-cyclopenta[b]furan was converted to 3,3abeta,4,5,6,6abeta-hexahydro-4beta-[3alpha-(2-tetrahydropyranyloxy-4-trifluoromethyl-4-methyl-1-trans-octenyl]-2-oxo-2H-cyclopenta[b]furan.

EXAMPLE 97

By the procedure of Example 83, 3,3abeta,4,5,6,6abeta-hexahydro-4beta-[3alpha-(2-tetrahydropyranyloxy)-4-trifluoromethyl-1-trans-octenyl]-2-oxo-2H-cyclopenta[b]furan is converted to 3,3abeta,4,5,6,6abeta-hexahydro-4beta-[3alpha-(2-tetrahydropyranyloxy)-4-trifluoromethyl-1-trans-octenyl]-2H-cyclopenta[b]furan-2-ol.

EXAMPLE 98

By the procedure of Example 83, 3,3abeta,4,5,6,6abeta-hexahydro-4beta-[3alpha-(2-tetrahydropyranyloxy)-4-trifluoromethyl-4-methyl-1-trans-octenyl]-2-oxo-2H-cyclopenta[b]furan was converted to 3,3abeta,4,5,6,6abeta-hexahydro-4beta-[3alpha-(2-tetrahydropyranyloxy)-4-trifluoromethyl-4-methyl-1-trans-octenyl]-2H-cyclopenta[b]furan-2-ol.

EXAMPLE 99

By the procedure of Example 85, 3,3abeta,4,5,6,6abeta-hexahydro-4beta-[3alpha-(2-tetrahydropyranyloxy)-4-trifluoromethyl-1-trans-octenyl]-2H-cyclopenta[b]furan-2-ol was converted to 7-(5alpha-hydroxy-2beta-[3alpha-(2-tetrahydropyranyloxy)-4-trifluoromethyl-1-trans-octenyl]-1alpha-cyclopentyl)-cis-5-heptenoic acid.

EXAMPLE 100

By the procedure of Example 85, 3,3abeta,4,5,6-,6abeta-hexahydro-4beta-[3alpha-(2-tetrahydropyranyloxy)-4-trifluoromethyl-4-methyl-1-trans-octenyl]-2H-cyclopenta[b]furan-2-ol was converted to 7-{5alpha-hydroxy-2beta-[3alpha-(2-tetrahydropyranyloxy)-4-trifluoromethyl-4-methyl-1-trans-octenyl]-1alpha-cyclopentyl}-cis-5-heptenoic acid.

EXAMPLE 101

By the procedure of Example 87, 7-{5alpha-hydroxy-2beta-[3alpha-(2-tetrahydropyranyloxy)-4-trifluoromethyl-1-trans-octenyl]-1alpha-cyclopentyl}-cis-5-heptenoic acid was converted to 7-{5-oxo-2beta-(3alpha-hydroxy-4-trifluoromethyl-1-trans-octenyl)-alpha-cyclopentyl}-cis-5-heptenoic acid.

EXAMPLE 102

By the procedure of Example 87, 7{-5alpha-hydroxy-2beta-[3alpha-(2-tetrahydropyranyloxy)-4-trifluoromethyl-4-methyl-1-trans-octenyl]-1alpha-cyclopentyl}-cis-5-heptenoic acid was converted to 7-[5-oxo-2beta-(3alpha-hydroxy-4-trifluoromethyl-4-methyl-1-trans-octenyl)-1alpha-cyclopentyl]-cis-5-heptenoic acid.

EXAMPLE 103

By the procedure of Example 89, 7-{5alpha-hydroxy-2beta-[3alpha-(2-tetrahydropyranyloxy)4-trifluoromethyl-1-trans-octenyl]-1alpha-cyclopentyl}-cis-5-heptenoic acid was converted to 7-[5alpha-hydroxy-2beta-(3alpha-hydroxy-4-trifluoromethyl-1-trans-octenyl)-1alpha-cyclopentyl]-cis-5-heptenoic acid.

EXAMPLE 104

By the procedure of Example 89, 7-{5alpha-hydroxy-2beta-[3alpha-(2-tetrahydropyranyloxy)-4-trifluoromethyl-4-methyl-1-trans-ocetnyl]-1alpha-cyclopentyl}-cis-5-heptenoic acid was converted to 7-[5alpha-hydroxy-2beta-(3alpha-hydroxy-4-trifluoromethyl-4-methyl-1-trans-octenyl)-1alpha-cyclopentyl]-cis-5-heptenoic acid.

EXAMPLE 105

A tablet was prepared containing the following ingredients:

|  | Per Tablet |
| --- | --- |
| 7-[3alpha-methyl-5-oxo-2beta-(3alpha-hydroxy-4-trifluoromethyl-1-trans-octenyl)-lalpha-cyclopentyl]-cis-5-heptenoic acid | 200 mg. |
| Dicalcium phosphate dihydrate, unmilled | 235 mg. |
| Corn starch | 70 mg. |
| FD&C Yellow #5 - Aluminum Lake 25% | 2 mg. |
| Durkee Duratex* | 25 mg. |
| Calcium stearate | 3 mg. |
| Total Weight | 535 mg. |

*Hydrogenated cotton seed oil (fully saturated)

All of the above ingredients were mixed until thoroughly blended in a suitable size container. The powder was filled into #2, two-piece, hard shell gelatin capsules to an approximate fill weight of 350 mg. using a capsulating machine.

EXAMPLE 106

A capsule was prepared by the procedure of Example 105 except that 7-[2beta-(4-trifluoromethyl-3alpha-hydroxy-1-trans-octenyl)-5-oxo-1alpha-cyclopentyl]-cis-5-heptenoic acid was the active ingredient.

EXAMPLE 107

A capsule was prepared by the procedure of Example 105 except that 7-[5alpha-hydroxy-2beta-(3alpha-hydroxy-4-trifluoromethyl-1-trans-octenyl)-1alpha-cyclopentyl]-cis-5-heptenoic acid was the active ingredient.

EXAMPLE 108

A tablet was found containing:

|  | Per Tablet |
| --- | --- |
| 7-[3alpha-methyl-5-oxo-2beta-(3alpha-hydroxy-4-trifluoromethyl-1-trans-octenyl)-lalpha-cyclopentyl]-cis-5-heptenoic acid | 25 mg. |
| Dicalcium phosphate dihydrate, unmilled | 175 mg. |
| Corn startch | 24 mg. |
| Magnesium stearate | 1 mg. |
| Total Weight | 225 mg. |

The 7-[3alpha-methyl-5-oxo-2beta-(3alpha-hydroxy-4-trifluoromethyl-1-trans-octenyl)-1alpha-cyclopentyl]-cis-5-heptenoic acid and corn starch were mixed together and passed through a #00 screen in Model "J" Fitzmill with hammers forward. This premix was then mixed with dicalcium phosphate and one-half of the magnesium stearate, passed through a #1A screen in Model "J" Fitzmill with knives forward, and slugged. The slugs were passed through a #2A plate in a Model "D" Fitzmill at slow speed with knives forward, and the remaining magnesium stearate was added. The mixture was mixed and compressed.

EXAMPLE 109

A tablet was formulated in the same manner as in Example 108 except that 7-[2beta-(4-trifluoromethyl-4-methyl-3alpha-hydroxy-1-trans-octenyl)-5-oxo-1alpha-cyclopentyl]-cis-5-heptenoic acid was the active ingredient.

EXAMPLE 110

A tablet was formulated in the same manner as in Example 108 except that 7-[5alpha-hydroxy-2beta-(3alpha-hydroxy-4-trifluoromethyl-1-trans-octenyl)-1alpha-cyclopentyl]-cis-5-heptenoic acid was the active ingredient.

EXAMPLE 111

To 750 ml of a 0.8 M solution of molybdenum hexafluoride in methylene chloride saturated with borontrifluoride was added at −30° 95 g of 2-keto hexanoic acid ethyl ester dissolved in 300 ml of methylene chloride. The resulting solution was allowed to warm to room temperature and stirred at this temperature for 3 hrs. The solution was then cooled to 0° and 500 ml of water was added. The methylene chloride solution was separated and washed with water, a sat. sodium chloride solution and a sat. sodium bicarbonate solution. The methylene chloride solution was dried ($MgSO_4$) and the solvent removed at atmospheric pressure. Distillation of the residue afforded 21 g of 2,2-difluoro hexanoic acid ethyl ester bp 73°-75° (23 mmHg).

EXAMPLE 112

Dimethyl-(2-oxo-3,4-difluoroheptyl)phosphonate

To a solution of 31.8 g of methyl dimethylphosphonate in 300 ml of dry THF was added with stirring at −78° 1 eq. of butyl lithium in hexane. After stirring for 0.5 hr. at this temperature, 21 g of 2,2-difluoro hexanoic acid ethyl esther was added and the mixture stirred at −78° for 1 hr. and then allowed to warm to 0°. Pentane (200 ml) and 4 N $H_2SO_4$ was added (pH 6) and the mixture separated. The aqueous phase was extracted with pentane and the organic layers combined and dried ($MgSO_4$). The solvent was removed under reduced pressure and the product purified via column chromatography. Distillation afforded 20.6 g of dimethyl (2-oxo-3,3-difluoroheptyl)phosphonate bp 108°–110° (0.4 mmHg).

EXAMPLE 113

3,3aR,4,5,6,6aS-Hexahydro-4R-(4,4-difluoro-3-oxo-1-trans-octenyl)-5R-methyl-2H-cyclopenta[b]furan-2-one By the procedure of example 7, 3,3aR,4,5,6,6aS-hexahydro-4S-formyl-5R-methyl-2H-cyclopenta[b]furan-2-one was reacted with dimethyl-(2-oxo-3,3-difluoroheptyl)phosphonate to give 3,3aR,4,5,6,6aS-hexahydro-4R-(4,4-difluoro-3-oxo-1-trans-octenyl)-5R-methyl-2H-cyclopenta[b]furan-2-one as a colorless viscous oil. Structure in agreement with mass spectrum.

EXAMPLE 114

3,3aR,4,5,6,6aS-Hexahydro-4R-(4,4-difluoro-3S-hydroxy-1-trans-octenyl)-5R-methyl-2H-cyclopenta[b]furan-2-one and
3,3aR,4,5,6,6aS-hexahydro-4R-(4,4-difluoro-3R-hydroxy-1-trans-octenyl)-5R-methyl-2H-cyclopenta[b]furan-2-one By the procedure of example 8, 3,3aR,4,5,6,6aS-hexahydro-4R-(4,4-difluoro-3-oxo-1-trans-octenyl)-5R-methyl-2H-cyclopenta[b]furan-2-one was converted to 3,3aR,4,5,6,6aS-hexahydro-4R-(4,4-difluoro-3S-hydroxy-1-trans-octenyl)-5R-methyl-2H-cyclopenta[b]furan-2-one mp 66°–67.5° and 3,3aR,4,5,6,6aS-hexahydro-4R-(4,4-difluoro-3R-hydroxy-1-trans-octenyl)5R-methyl-2H-cyclopenta[b]furan-2-one a light yellow viscous oil. The mass spectra data is in agreement with the structures indicated.

EXAMPLE 115

3,3aR,4,5,6,6aS-Hexahydro-4R[4,4-difluoro-3R-(tetrahydro-2H-2-pyranyloxy)-1-trans-octenyl]-5R-methyl-2H-cyclopenta[b]furan-2-one By the procedure of example 9, 3,3aR,4,5,6,6aS-hexahydro-4R-(4,4-difluoro-3R-hydroxy-1-trans-octenyl)-5R-methyl-2H-cyclopenta[b]furan-2-one was converted to 3,3aR,4,5,6,6aS-hexahydro-4R[4,4-difluoro-3R(tetrahydro-2H-2-pyranyloxy)-1-trans-octenyl]-5R-methyl-2H-cyclopenta-[b]furan-2-one a light yellow viscous oil. The mass spectra is in agreement with the structure indicated.

EXAMPLE 116 nat.(2,E)-11R-Methyl-16,16-difluoro-15R-(tetrahydro-2H-2-pyranyloxy)-9S-hydroxyprosta-5,13-dienoic acid By the procedure of example 9, 3,3aR,4,5,6,6aS-hexahydro-4R-[4,4-difluoro-3R-(tetrahydro-2H-2-pyranyloxy)-1-trans-octenyl]5R-methyl-2H-cyclopenta[b]furan-2-one was converted to 3,3aR,4,5,6,6aR-hexahydro-4R-[4,4-difluoro-3R-(tetrahydro-2H-2-pyranyloxy)-1-trans-octenyl]5R-methyl-2H-cyclopenta[b]furan-2-ol.

By the procedure of example 10, 3,3aR,4,5,6,6aS-hexahydro-4R-[4,4-difluoro-3R-(tetrahydro-2H-2-pyranyloxy)-1-trans-octenyl]5R-methyl-2H-cyclopenta-[b]furan-2-ol was converted to nat.(2,E)-11R-methyl-16,16-difluoro-15R-(tetrahydro-2H-2-pyranyloxy)-9S-hydroxyprosta-5,13-dienoic acid a light yellow viscous oil. The mass spectra data is in agreement with the structure indicated.

EXAMPLE 117 nat.(2,E)-11R-Methyl-16,16-difluoro-9S,15R-dihydroxyprosta-5,13-dienoic acid

By the procedure of example 11, nat.(2,E)-11R-methyl-16,16-difluoro-15R-(tetrahydro-2H-2-pyranyloxy)-9S-hydroxyprosta-5,13-dienoic acid was converted to nat.(2,E)-11R-methyl-16,16-difluoro-9S,15R-dihydroxyprosta-5,13-dienoic acid a light yellow viscous oil. The mass spectra is in agreement with the structure indicated.

EXAMPLE 118 nat.(2,E)-11R-Methyl-16,16-difluoro-15R-hydroxy-9-oxoprosta-5,13-dienoic acid

By the procedure of example 12, nat.(2,E)-11R-methyl-16,16-difluoro-15R-(tetrahydro-2H-2-pyranyloxy)-9S-hydroxyprosta-5,13-dienoic acid was converted to nat.(2,E)-11R-methyl-16,16-difluoro-15R-hydroxy-9-oxoprosta-5,13-dienoic acid a light yellow viscous oil, $[\alpha]_D^{25} - 67.76$ ($CHCl_3$).

Calc.: C 65.26, H 8.35, F 9.83; Found: C 65.46, H 8.47, F 9.60.

We claim:

1. A compound of the formula:

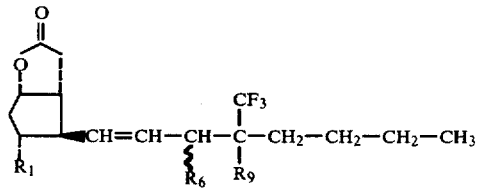

wherein $R_1$ is —$COOR_1'$; lower alkyl or $CH_2OR_1'$; $R_1'$ is hydrogen or lower alkyl; $R_6$ is hydroxy or hydroxy protected with a hydrolyzable ether or ester group; $R_9$ is hydrogen, lower alkyl or fluoro; or enantiomers or racemates thereof.

2. The compound of claim 1 wherein $R_9$ is hydrogen or lower alkyl.

3. The compound of claim 2 wherein said compound is 3,3abeta,4,5,6,6beta-hexahydro-4beta-[3alpha-(2-tetrahydropyranyloxy)-4-methyl-4-trifluoromethyl-1-trans-octenyl]-5alpha-methyl-2-oxo-2H-cyclopenta[b]furan.

4. The compound of claim 2 wherein said compound is 3,3abeta,4,5,6,6abeta-hexahydro-4beta-[3alpha-(2-tetrahydropyranyloxy)-4-trifluoromethyl-1-trans-octenyl]-5alpha-methyl-2-oxo-2H-cyclopenta[b]furan.

5. An optically active salt of the formula wherein $R_{27}$ is

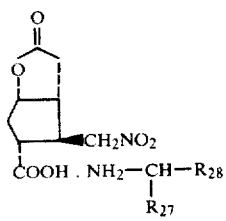

$$-\overset{OH}{\underset{|}{CH}}-R_{29},$$

tolyl, naphthyl or phenyl, or naphthyl or phenyl substituted with amino, nitro or halo; $R_{29}$ is tolyl, naphthyl or phenyl, or naphthyl or phenyl substituted with amino, nitro or halo; $R_{28}$ is $CH_2R_{31}$; and $R_{31}$ is hydrogen, lower alkyl, hydroxy or lower alkoxy or its optically active compounds.

6. The optically active salt of claim 5 wherein $R_{28}$ is methyl and $R_{27}$ is p-nitrophenyl.

* * * * *